United States Patent
Fitzsimmons et al.

(10) Patent No.: US 10,078,096 B2
(45) Date of Patent: Sep. 18, 2018

(54) COMPUTER ASSISTED ERGONOMIC WORKSTATION DESIGNS AND METHODS

(71) Applicant: Fitzsimmons and Associates, Oakland, CA (US)

(72) Inventors: John Fitzsimmons, Oakland, CA (US); Alexander Kouznetsov, Danville, CA (US)

(*) Notice: Subject to any disclaimer, the term of this patent is extended or adjusted under 35 U.S.C. 154(b) by 812 days.

(21) Appl. No.: 14/519,797

(22) Filed: Oct. 21, 2014

(65) Prior Publication Data

US 2015/0142381 A1     May 21, 2015

Related U.S. Application Data

(63) Continuation of application No. PCT/US2014/051430, filed on Aug. 18, 2014.

(60) Provisional application No. 61/876,870, filed on Sep. 12, 2013, provisional application No. 61/867,231, filed on Aug. 19, 2013.

(51) Int. Cl.
| | |
|---|---|
| *G01P 15/00* | (2006.01) |
| *A47C 3/20* | (2006.01) |
| *A47C 31/12* | (2006.01) |
| *A47C 7/00* | (2006.01) |
| *G06F 19/00* | (2018.01) |

(52) U.S. Cl.
CPC .......... *G01P 15/00* (2013.01); *A47C 3/20* (2013.01); *A47C 7/006* (2013.01); *A47C 31/126* (2013.01); *G06F 19/3481* (2013.01)

(58) Field of Classification Search
CPC .......... G01B 21/16; G01B 21/02; A47C 3/20; G01P 15/00
USPC .......................................... 702/166; 700/275
See application file for complete search history.

(56) References Cited

U.S. PATENT DOCUMENTS

| | | | |
|---|---|---|---|
| 8,195,475 B1 | 6/2012 | Landsman et al. | |
| 8,928,484 B2* | 1/2015 | Chang | A61B 5/0002 340/573.1 |
| 9,024,976 B2* | 5/2015 | Leuthardt | A61B 5/0002 345/660 |

(Continued)

OTHER PUBLICATIONS

"Yanyan", "Accelerometer Sensor Data Processing", Jan. 1, 2013, "Sensibility Testbed" https://seattlesensor.wordpress.com/2013/01/01/accelerometersensordataprocessing/.*

(Continued)

*Primary Examiner* — Stephanie Bloss
(74) *Attorney, Agent, or Firm* — D. Benjamin Borson; Borson Law Group PC

(57) ABSTRACT

Aspects of this invention include new measures of hip-torso posture and strength of the legs. These new measures are made using new tools. Measurement of hip-torso posture can be made using simple tools. One such tool can be applied to the hips, and indicates relative angle of the spine. Photographic tools can be used to analyze posture relative to vertical references. Measurement of leg strength can be made using a device incorporating accelerometers and computer implemented instructions to quantify forward/backward, left/right, or rotational acceleration when the legs are challenged. Other aspects include devices with computer implemented instructions to quantify leg strength. Using the new devices and methods, one can objectively determine postures that are ergonomically appropriate for persons sitting and working at workstations.

17 Claims, 20 Drawing Sheets

(56) References Cited

U.S. PATENT DOCUMENTS

| | | | |
|---|---|---|---|
| 2010/0066132 A1* | 3/2010 | Tal Marchand | A47B 83/02 297/170 |
| 2010/0094645 A1* | 4/2010 | Carroll | G06Q 50/24 705/2 |
| 2011/0055720 A1* | 3/2011 | Potter | G06F 3/017 715/747 |
| 2011/0263950 A1* | 10/2011 | Larson | A61B 5/1113 600/301 |
| 2013/0244211 A1* | 9/2013 | Dowling | G06F 19/3481 434/247 |
| 2013/0331993 A1* | 12/2013 | Detsch | G05B 15/02 700/275 |

OTHER PUBLICATIONS

Written Opinion, dated Feb. 23, 2016, Fitzsimmons.

F. Gerr, et al, A randomized controlled trial of posturla interventions for prevention of musculoskeletal symjptoms among computer users. Occup. Environ Med 2005, 62:478-487. doi. 10.1136/oem. 2004.015792.

Burnett A, O'Sullivan P, Caneiro JP, Krug R, Bochmann F, Helgestad GW (2009) An examination of the flexion-relaxation phenomenon in the cervical spine in lumbo-pelvic sitting. Journal of Electromyography and Kinesiology 19 (2009) e229-e236.

Herd C, Meserve B. (2008). A systematic review of the effectiveness of manipulative therapy in treating lateral epicondylalgia. Journal of Manual and Manipulative Therapy. 16(4): 225-237.

Vicenzio B, Cleland JA, Bisset L. Joint manipulation in the management of lateral epicondylalgia: A clinical commentary. J Man Manip Ther 2007;15:50-6.

Caneiro JP, O'Sullivan P, Burnett A, Barach A, O'Neil D, Tveit O, Olafsdottir K (2010) The influence of different sitting postures on head/neck posture and muscle activity. Man Ther 15(1):54-60.

Falla D, Jull G, Russell T, Vicenzino B & Hodges P. Effect of neck exercises on sitting posture in patients with chronic neck pain. J Physical Therapy. 2007; 87: 408-16.

Pynt, Jenny, Joy Higgs, and Martin Mackey. Seeking the optimal posture of the seated lumbar spine. Physiotherapy Theory and Practice 17, No. 1 (2001): 5-21.

Wilke HJ, Neef P, Caimi M, Hoogland T, Claes LE (1999) New in vivo measurements of pressures in the intervertebral disc in daily life. Spine 24: 755-762.

* cited by examiner

FIG. 15       1500

COMPUTER ASSISTED ERGONOMIC WORKSTATION DESIGNS AND METHODS

CLAIM OF PRIORITY

This application claims priority to U.S. Provisional Patent Application No. 61/867,231 filed Aug. 19, 2013, entitled "Computer Assisted Ergonomic Workstation Designs and Methods," John Fitzsimmons and Alex Kouznetsov inventors, and U.S. Provisional Patent Application No. 61/876,870 filed Sep. 12, 2013, entitled "Computer Assisted Ergonomic Workstation Designs and Methods," John Fitzsimmons and Alex Kouznetsov inventors. Both of these provisional applications are incorporated herein fully by reference.

FIELD OF THE INVENTION

This invention relates to improvements in the design of ergonomically efficient workstations. Particularly, this invention relates to improved computer assisted methods for creating ergonomically efficient seated workstations. More particularly, this invention relates to use of mobile computing devices to assist in creation of ergonomically efficient designs based on new metrics using new tools, one for measuring hip-spine position to identify and optimize spinal postures, and another for analyzing leg strength to optimize chair height.

BACKGROUND

Modern sitting workstations typically involve a person, seated in a chair, stool or other device that is placed near to a table, computer desk, keyboard, and screen, termed herein "workstations." Although such systems have been and are increasingly used world-wide, and currently represent one of the most significant features of modern enterprise, little has been done to improve the efficiency of design of placement of objects in workstations.

SUMMARY

Prior approaches used in designing ergonometric workstations have used anthropometric landmark data to locate body postures at workstations, and as a result, many individuals who spend significant time working at such workstations experience back pain, leg pain, neck pain, wrist and hand pain, and other disorders. Some approaches to resolve such problems involve use of adjustable chairs, stools, desks, and keyboards. However, many of these efforts are based simply upon "trial and error" in making adjustments, or focus on the position of the extremities rather than directly manage spinal postures.

We have identified a new problem in the art, namely, the lack of objective measures individualized to each person at a workstation.

This invention solves the problem by identifying key postural indicators that enable, for the first time, objective measurements of an individual's spinal posture and body positions while at a workstation. With the use of new tools and metrics, we have created substantial improvements in ergonomic designs.

Thus, in certain aspects, this invention can take advantage of current mobile technology, involving such devices as "Smart Phones," including iPhones®, "Android® systems, and other such mobile devices. These devices typically have an accelerometer as a built-in feature. Certain aspects of this invention use data obtained from accelerometers transmitted to a computer processor, to measure physiologic parameters. Additionally, certain aspects of this invention, very simple devices can be designed, built, and programmed to serve similar functions.

In some of these or other aspects, computer-implemented software programs are designed to use data obtained from accelerometers to measure leg movements, and leg strength while a person is at a workstation. Using this information, aspects of this invention determine a metric using a new tool for determining hip-spine position, "HIPINDIX™" (a trademark of Fitzsimmons & Associates, Oakland Calif.). The hip-spine tool is used to show pelvic rotation, and maximum leg strength is measured using a software application, such as a "HIPTORQUE™" tool (a trademark of Fitzsimmons & Associates, Oakland, Calif.).

In additional aspects, computer implemented photographic methods can be used to analyze seated postures. In some of these aspects, one can use a HIPPIC™ tool (a trademark of Fitzsimmons & Associates, Oakland, Calif.).

The new metrics differ from prior metrics in that instead of relying upon measured angles of legs, this aspect of the invention focuses on the pelvis position and leg strength. The idea of focusing on the pelvis is based on the relationship between the legs, hip joint, shoulder joint, torso, arms, neck and other body parts that form a unified support for the person seated at a workstation. If the lumbar spine is under flexion or extension stress, other body parts will attempt to compensate for the stress, and may themselves be subjected to undesirable stresses, which can lead to pain or other dysfunctions. By identifying body postures that are "neutral" for the lower back (the lumbar spine), and adjusting the configuration of objects in the workstation, stresses on the lumbar vertebrae can be minimized, the overall posture more aligned with gravity, and thereby decreasing injury risk factors on other portions of a person's body. Improved posture can reduce injury risk factors and lower symptoms of pain and dysfunction, improving performance.

Aspects

Some aspects of this invention are listed below. In general, particular aspects can be combined with other aspects, either singularly or in multiple combinations.

Aspect 1. A method for determining chair height of a subject seated in a chair at a workstation, comprising the steps:

a. providing a mobile computing device, having a processor, a memory, a plurality of accelerometers; and a display;
  b. affixing said mobile computing device to said chair:
  c. adjusting the height of said chair to a first height;
  d. instructing said subject to sit in said chair and rapidly move the chair using said subjects legs placed on the floor;
  e. determining the maximum acceleration achieved during said moving in step d;
  f. adjusting the height of said chair to a second height;
  g. repeating steps d and e;
  h. adjusting the height of said chair to a third height;
  i. repeating steps d and e; and
  j. displaying on the display, the maximum accelerations achieved versus chair height.

Aspect 2. The method of Aspect 1, where said determining maximum acceleration in step e is carried out by said processor programmed to perform the steps:

i. said accelerometers providing gravity data for three dimensions of motion, an "X" dimension, a "Y" dimension, and a "Z" dimension, each of said dimensions being perpendicular to each of the other dimensions, said data being "gravX", "gravy", and "gravZ", respectively, each expressed as the effective gravitational acceleration in each of said dimensions;

ii. sampling said gravity data at a frequency of about 1 time per second to about 40 times per second, and storing said data in said memory;

iii. updating said gravX, gravy and gravZ values where said updated values are calculated according to the following formulas:

$$gravX = alpha*gravX + (1-alpha)*ev.x;$$

$$gravY = alpha*gravY + (1-alpha)*ev.y;$$

$$gravZ = alpha*gravZ + (1-alpha)*ev.z;$$

where alpha is a time interval for a low pass filter, ev.x, ev.y, and ev.z are new gravity data in the X, Y, and Z dimensions respectively. Generally, alpha is between zero (0) and one (1). Preferably, alpha is between 0.1 and 0.9, more preferably between 0.2 and 0.8, still more preferably between 0.3 and 0.7, even more preferably between 0.4 ad 0.6, and yet more preferably 0.5;

iv. calculate acceleration by removing the gravity contribution using a high-pass filter according to the following formula:

$$accX = ev.x - gravX;$$

$$accY = ev.y - gravY;$$

$$accZ = ev.z - gravZ,$$

where accZ, accY, and accZ are accelerations in the X, Y, and Z dimensions, respectively; and v. calculating for each time point, total linear acceleration ("A") according to the formula:

$$A = (accX^2 + accY^2 + accZ^2)^{1/2}; \text{ and}$$

vi. storing said values of A in said memory.

Aspect 3. The method of any preceding Aspect, where sampling rate of said gravity data is a frequency of about 10 times per second.

Aspect 4. A method for determining optimum chair height of a subject seated in a chair at a workstation, comprising: determining the height of said chair that produces the maximum acceleration according to Embodiment 1, step j.

Aspect 5. The method of any preceding Aspect, further comprising the steps: establishing proper chair/caster/floor conditions; and confirming neutral spine posture.

Aspect 6. The method of any preceding Aspect, further comprising the steps: measuring the height of the elbow and the eye of said subject; and providing a keyboard tray at a location that maintains neutral spine posture.

Aspect 7. The method of any preceding Aspect, further comprising the steps:
determining maximum acceleration as for step e of Embodiment 1 calculated for a first seat pan angle; and
changing said seat pan angle to a second pan angle and repeating said step e of Aspect 1.

Aspect 8. The method of any preceding Aspect, where said step of confirming neutral spine posture is carried out by measuring the angle inscribed by a first line connecting a lateral point on said subject's waist over the lumbar spine and said subject's shoulder, and a second line connecting a lateral point on said subjects waist over the lumbar spine to said subject's ear, where said angle inscribed is less than about 20 degrees.

Aspect 9. The method of any preceding Aspect, where said step of confirming neutral spine posture is carried out by the steps:
i taking a photograph of said subject seated in said chair; and
ii comparing the angle inscribed between a vertical line from said floor and a line connecting a lateral point on said subject's waist over the lumbar spine and said subject's ear, where said angle inscribed is less than about 15 degrees.

Aspect 10. a mobile computing device comprising:
at least two accelerometers (X and Y dimensions), and preferably three accelerometers (X, Y, and Z dimensions);
a memory storage module;
a user interface;
a display; and
a computer processor containing programming instructions for carrying out the following steps:
i. accepting data from accelerometers providing gravity data for two or three dimensions of motion, an "X" dimension, a "Y" dimension, and optionally, a "Z" dimension, each of said dimensions being perpendicular to each of the other dimensions, said data being "gravX", "gravy", and "gravZ", respectively, each expressed as the effective gravitational acceleration in each of said dimensions;
ii. sampling said gravity data at a frequency of about 1 time per second to about 40 times per second, and storing said data in said memory;
iii. updating said gravX, gravy and gravZ values where said updated values are calculated according to the following formulas:

$$gravX = alpha*gravX + (1-alpha)*ev.x;$$

$$gravY = alpha*gravY + (1-alpha)*ev.y;$$

$$gravZ = alpha*gravZ + (1-alpha)*ev.z;$$

where alpha is a time interval for a low pass filter, ev.x, ev.y, and ev.z are new gravity data in the X, Y, and Z dimensions respectively. Generally, alpha is between zero (0) and one (1). Preferably, alpha is between 0.1 and 0.9, more preferably between 0.2 and 0.8, still more preferably between 0.3 and 0.7, even more preferably between 0.4 ad 0.6, and yet more preferably 0.5;

iv. calculate acceleration by removing the gravity contribution using a high-pass filter according to the following formula:

$$accX = ev.x - gravX;$$

$$accY = ev.y - gravY;$$

$$accZ = ev.z - gravZ,$$

where accZ, accY, and accZ are accelerations in the X, Y, and Z dimensions, respectively; and v. calculating for each time point, total linear acceleration ("A") according to the formula:

$$A = (accX^2 + accY^2 + accZ^2)^{1/2}; \text{ and}$$

vi. storing said values of A in a memory of the device.

Aspect 11: A device of Aspect 10, where a processor can also be programmed to display acceleration values versus chair height and/or acceleration values versus chair pan angle.

Aspect 12: A method according to any preceding Aspect, where the parameters of a low-pass filter and/or a high-pass filter are adjusted to permit acquisition of accurate information about small, periodic motions, by avoiding either over-damping or under-damping.

BRIEF DESCRIPTION OF THE DRAWINGS

This invention is being described with reference to specific embodiments thereof. Other features of this invention can be appreciated with reference to the Figures, in which.

DETAILED DESCRIPTION

Figure 1A:
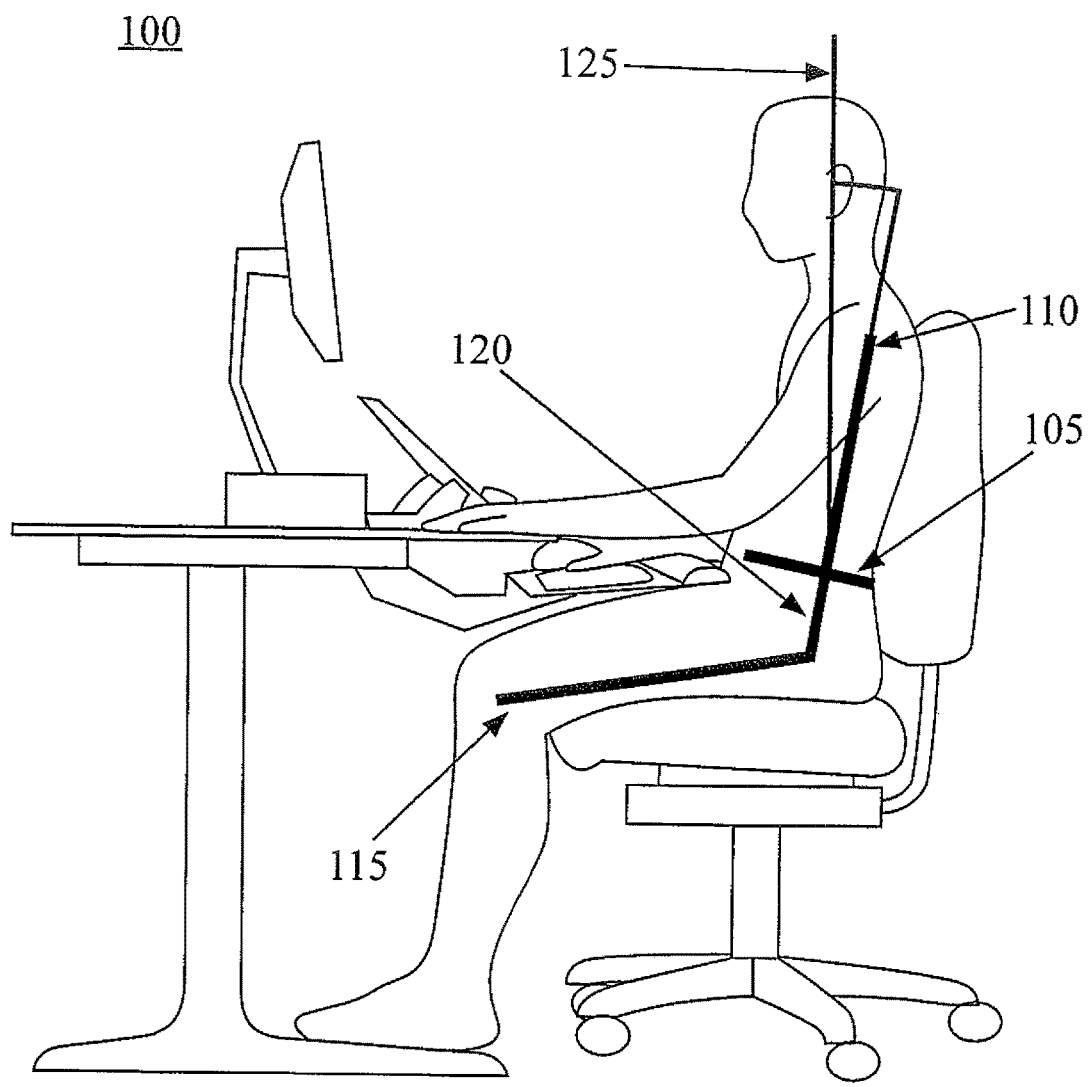
FIG. 1A depicts a drawing of a user seated at a workstation with a suitable reclined posture.

Clinical evidence supports the idea that neutral lumbar spine postures are preferred for sitting; (Pynt, J., Higgs, J., & Mackey, M., Seeking the optimal posture of the seated lumbar spine. *Physiotherapy Theory and Practice* 17, 5-21 (2001)). Additionally, adverse spinal postures may contribute to cumulative trauma in the upper extremities; (Herd, C., & Meserve, B. A systematic review of the effectiveness of manipulative therapy in treating lateral epicondylalgia. *Journal of Manual and Manipulative Therapy* 16, 225-236 (2008). Vicenzino, B., Cleland, J., & Bisset, L. Joint manipulation in the management of lateral eipcondylalgia: A clinical commentary. *Journal of Manual and Manipulative Therapy* 15, 50-56(2007). Waugh, E., Jaglal S., Davis, A, Tomlinson, G., & Verrier, M. Factors associated with prognosis of lateral epicondylitis after 8 weeks of physical therapy. *Archives of Physical Medicine Rehabilitation* 85, 308-318 (2004)).

Moreover, slumped position of the lumbar spine affects the posture of the neck; Falla. D., O'Leary, S., Fagan, A., & Jull, G. Recruitment of the deep cervical flexor muscles during a postural-correction exercise performed in sitting. *Manual Therapy* 12, 139-143 (2007). Burnett, A., O'Sullivan, P., Caneiro, J., Krug, R., Bochmann, F., & Helgestad, G. An examination of the flexion-relaxation phenomenon in the cervical spine in lumbo-pelvic sitting. *Journal of Electromyography and Kinesiology* 19, 229-236 (2009). Caneiro, J., O'Sullivan, P., Burnett, A., Barach, A., O'Neil, D., Tveit, O., & Olafsdottir, K., The influence of different sitting postures on head/neck posture and muscle activity. *Manual Therapy* 30, 1-7 (2009)).

All of these problems can lead to increased morbidity and loss of function of affected portions of the body.

Slumping at the spine increases the user's exposure to a greater risk of injury of the low back and the neck, and increases likelihood of secondary injury to the shoulders, arm and hands. Current ergonomic strategies use specific angle measures for the extremities as an indirect determinant of optimal postures, and because they do not adequately represent spinal posture, those strategies present a greater risk of injury for some tasks.

Current ergonomic strategies use methods that approximate idealized angles for the extremities in hypothetical work postures, but do not accommodate or identify work demands that may change spinal postures from what the chair adjustment may predict. Reliance upon such idealized angles may not account for differences between individuals, such as height, weight, relationships between leg length and torso length, arm length, neck length and the like, which can significantly change the relationship with workstations of standardized dimensions. In aspects of this invention, specific work demands can be more useful determinants of spinal posture than chair adjustment. Slumping results when (reclined) chair adjustment does not agree with the nature of the (forward) work required. When chair adjustment and work requirements do not agree, a slump-seated posture can result when work is sustained over time.

These observations and deficiencies have not been adequately addressed before this invention.

Moreover, there have been no disclosures of how to modify existing chair adjustment to improve spinal posture based on hip and pelvis position in relation to the remainder of the user's body, nor does it provide for any changes to chair-workstation positions that optimize postural support and movement.

Embodiments of the Invention

The instant application discloses new and non-obvious strategies for addressing these problems.

System and Method for Observing and Supporting Ergonomic Posture

Systematic strategies are presented to observe and optimize spinal postures in sitting, which can be substantiated with new measurement devices, including accelerometers and photographic methods. The systems and methods include objective measures of leg strength and hip-spine position.

Measurement of Leg Strength

One can use objective measures of leg strength to determine desired seat positions using either or both of a "dynamic" method or a "static" method.

Use of Leg Strength to Determine Neutral Posture of the Spine

In some aspects, measurements of leg strength in a sitting position with neutral spine posture can be a used to determine chair height with leg support, locate proper Arm support height of a work surface height, place a visual target, and determine a reach distance based on the desired posture. The prior art did not fully appreciate the roles of position, movement, and strength of the legs for their contributions to seated posture, particularly with a neutral spine position. Because the legs move and stabilize the pelvis as the foundation for spinal posture, analysis of leg strength and movement can be useful in promoting proper posture, and better support the position of a person at a workstation. A sequence of observations and measures can clarify workstation dimensions, following criteria for optimal seated posture.

Aspects of this invention can use data on motion of the body obtained using accelerometers connected to a computerized device, such as a smart phone, iPhone, Android, or other small device. Such devices can be attached to a chair at chair arm, seat, or other convenient location. Data from an accelerometer is input into a computerized processor programmed to provide an output to a display device, including the screen of a small device, or to a more centralized desktop or laptop computer. Using software and indicators of this invention, such data can be used to determine positions at which the body posture is easiest to maintain in neutral, with respect to gravity. Generally, it can be desirable to select body positions that provide for the maximum leg strength tested in functional directions, including forward-backward motion, side-to-side motion of the chair, and flexion and extension of the spine.

Aspects of this invention provide a decision sequence of observation, measurement and analytical steps to determine the priority by which optimal spinal posture is established in sitting, using the subject's leg and torso strength and spine position determined by pelvic sagittal rotation as primary measures to choose chair adjustment and furniture support specific for the client stature and work task. The process is designed to allow a user to engage the largest muscle groups for the safest, easiest and strongest posture for upright, seated work. In certain embodiments, one can use accelerometers to measure leg strength and chair motion (Dynamic Method) and in other embodiments, one can measure the force generated by the legs to maintain the body steady under conditions of load (Static Method).

Dynamic Method

Some embodiments of this invention include sensitive measures of the strength of the legs or torso. A device containing one or more accelerometers is used to collect data of accelerations of a chair, stool or other seating product, comparing different values for the acceleration of the chair at different heights to determine where the legs are strongest, and thereby allow the legs to best support the pelvis and working torso. Many subjects consistently identify their best height in a consistent manner by choosing one of several that feels best. As used herein the tem "acceleration" means both increase in speed and slowing of speed (also known as "deceleration"). This method suffers from problems associated with long-term work in non-ideal posture. A person may simply "get used to" a bad position, and may feel uncomfortable changing posture. Embodiments of this invention can be used to help a person understand how good posture can improve quality of work and decrease symptoms of poor postures.

A general guide will be when the body can change or correct position in the chair using hip and leg movement, before the chair moves. It is important to provide moderate resistance for chair movement over the floor: typically using carpet casters on a chair used on low-cut pile carpet, or hard-floor casters when the chair is used on linoleum, stone or hardwood. When the full range of chair height from "too high," to "too low" is presented, some users may make a subjective selection without any objective measure. Such decisions may lead to physiological dysfunction, pain, and other abnormalities, especially if such subjective postures are maintained for long periods of time. Therefore, useful applications of measures of leg strength and/or pelvis posture include analyzing ergonomic configurations when the required task requires forceful movement of the shoulder and arm, and resisted arm movements can be tested combined with leg strength, looking for the least movement of the chair (static model) rather than how easily the chair is moved according to a dynamic model, or when there are confounding variables, like several different shoe heights, multiple users or differences in the chair designs to be compared.

In the most basic form, leg strength or pelvis position can determine the acceleration of a chair in two horizontal planes, forward/backward and left/right (x- and y-axes), and diagonal patterns ("dynamic" method). Tools of this invention record the acceleration values for the sample set obtained at a first seat position. Additional sample sets can be collected by recording accelerations with different seat positions. Each data set should be identified with the chair height measured, keeping the chair-floor rolling resistance and the chair height and pan angle consistent during each of the samples used for comparison with values from the same subject. The subject posture should also be consistent during each sample: the subject sits upright on the middle of the level pan with the hands in the lap. The highest average value for the acceleration of the chair when the dynamic model is used can be desired. Although unlikely, a slightly higher or lower chair height (less than one inch) than that showing best leg strength may be selected to provide a more desirable position for reasons like leg pain or the close accommodation of work surface height.

Accelerations produced by the legs is calculated by the well known formula: $F=MA$, where F is force, M is mass, and A is acceleration. As applied to seated postures, the mass of the body is relatively constant, then acceleration values equal the force generated during the movement of the chair; the acceleration measures can be taken at different heights of the chair, and in certain embodiments, the optimal height is the height where the legs can generate the greatest force. Chair height can be adjusted to determine where the greatest acceleration can be generated by the force of the legs in a consistent pattern of chair pan angle, hip and knee angle and foot position.

Acceleration (in meters/sec per sec, or $m/sec^2$) values in the x, y, and diagonal directions are measured and entered into a computer memory for processing. In general, the processor takes each measured acceleration, squares it to avoid having negative values added to positive values, thereby cancelling out some data. The squared accelerations are added together and the square root of the sum is calculated and stored in memory. The height of the seat is changed, and a new set of acceleration values is captured, squared, summed, and the square root of the result is stored. To reduce the spurious effects of random or small motions, a minimum threshold for storing acceleration can be set by the user. If a particularly measured acceleration is less than the threshold, it is not stored. This can reduce the effect of random, or minor motions on the calculated maximal acceleration. In some cases, this threshold can be set to discard acceleration values of less than 0.001 $m/sec^2$, 0.1 $m/sec^2$, 0.2 $m/sec^2$, 0.3 $m/sec^2$, 0.4 $m/sec^2$, 0.5 $m/sec^2$, or any other selected value.

After a series of such tests for a subject, a graphical display of acceleration values obtained at each seat height can be plotted against the height of the seat. For example, a graphical User Interface (UI) can display acceleration in the vertical axis and seat height on the horizontal axis. Once the data has been displayed, a user can select the desired seat height that produces an acceleration at or near the position that produces the maximum acceleration. In some cases, it can be desired to set the seat position at the height that produces the maximum acceleration. It can be appreciated that in some situations, a single large acceleration may be observed, that is not generally representative of the subject's best seat position. Therefore, one can assess not only the maximum acceleration, but an average, mean, or mode of 2, 3, 4, 5 or more separate accelerations to determine a selected seat height.

One can also repeat the dynamic method under several different conditions of floor resistance (e.g., carpeted or bare floor), casters locked, chair axis locked, or other configurations, and select a seat height that reflects the user's working conditions.

However, depending on other factors, the seat height can be set to be within about 5%, 10%, 15%, 20% or 30% of the height that produced the maximum acceleration value.

In some embodiments, a subject's desired ergonomic configuration can be evaluated according to one or more of the following.
1. The chair caster type should be compatible with the type of floor surface, position the seat pan flat, position subject in upright sitting, with minimal arm support or back support.
2. The subject prepares to move the chair front-back and side-side, using the leg strength with the feet firmly on the floor.
3. Start the HIPTORQUE™ application, loaded onto a smart phone, (e.g., an iPhone or Android device attached to the chair.
4. Enter chair heights into the HIPTORQUE™ application database, either:
   a. Manually entered as a number (inches or centimeters) for each chair height tested, using a chair landmark that approximates the height for the bottom of the ischial tuberosities on the chair, and measure the vertical distance to the floor; or
   b. Chair height is automatically entered and calculated using additional automatic chair height sensors, calibrated (for pneumatic cylinder compression and position, or mechanical height), connected with the enhanced accelerometer(s) and processor(s) software using wireless methods (e.g., Bluetooth™), hard-wire, or radiofrequency (RF) communication.
5. Sample and collect data for each chair height.
   a. Sample size for each chair height is determined either by the software when data collection stops, or by sample of convenient duration determined by the investigator.
   b. The chair height range measured should include heights that are subjectively identified as "too low," and "too high."
   c. Ask the subject to identify and the investigator should record the height that feels best, meaning the chair seems to move most easily, and the height is most comfortable.
6. Each chair height test can have at least one sample set of data collected for acceleration measures; those data are recorded at the sample frequency for the accelerometer, and collected either for the length of time determined by convenience, observation of the investigator, or determined by the processor as a sufficient sample time, or determined by the processor as a set sample size (subject may deliver inconsistent attempts at movement that may not generate consistent samples for any given amount of time).
7. Every acceleration datum sampled for a specified chair height is squared to normalize acceleration and deceleration values, and those values are added to provide either: a) a gross acceleration value for the indicated chair height and leg strength, and/or b) numbers averaged to indicate a normalized acceleration value for that chair height.
8. The five highest acceleration values, or the five lowest acceleration values for each of five chair heights will be displayed, depending on the protocol selected.
9. Select the optimal chair height based on the strategy intended to test leg torque:
   a. Use the maximum acceleration values if chair movement is tested using a dynamic method
   b. Use the minimal values of acceleration if the legs are challenged to maintain a stable chair during resisted movements of the arms or other body parts.
10. The following data are recorded:
   a. manually recorded and the subject profile is completed for ID, anthropometry, including seat height, elbow height, eye height; work surface height and monitor height are also implied from these data;
   b. automatically recorded by the HIPTORQUE™ application on the cellphone or accelerometer/processor device, and stored as a client profile in the device.
   c. imported to a second dedicated database (PROFile, via IP address from the cell phone/accelerometer, downloaded by USB port or transferred with appropriate radio frequency.
11. Data from seat height measures can also be compared with the user's selected work surface heights and eye height that are measured manually, and manually input to the database, or in the case of electric height adjustable tables with IP address, concurrent data collection for use patterns through the day can be automatically recorded and processed. For example, the chair movement should be greatest when the seated work surface height is optimal; heights above and below optimal are not expected to reflect frequent chair movement. The amount of time in sitting and standing, and moving from sit-stand, and the reverse, can be recorded by the height of the table, and if that data is linked to same-time chair acceleration, the subjective choice of work surface height should agree with the maximum chair acceleration.

12. Seating strategies may consist of comparing long-term subjective data that was recorded from the subject reporting their "best height," with objective numbers recorded from acceleration data.

13. The skill to reliably record consistent subject measures and choose workstation dimensions can be demonstrated with documented training and practice, and certification may require nothing more than demonstrated academic and practical competence with the methods described above. Outcome measures for follow-up measures and alternative metrics will enhance that practice. Consistent, certified practice should correlate with long-term subjective results, compared for client productivity, symptom reports, injury rates, return on investment and general satisfaction used as a criteria for certification processes for consultants or to measure varied research strategies.

14. In addition, the peak torque curve may not be consistent between subjects, particularly for unusual seated tasks that require greater strength of longer duration: truck-tractor, tank, crane operations; pilots, race cars, etc.

15. The torso and leg strength, and the functional capacity and endurance will vary between subjects.

16. The percentage of subject's total strength required to move the chair will be greater in those who have a lower functional capacity, and the nature of forces that affect the peak of the curve can have a desirable effect.

17. The amount of peak acceleration generated and the consistency of that strength will show a range of values that inform additional ergonomic decisions about how to consider the location of the work surface height. When acceleration is plotted against chair height, the best height will show the highest acceleration, and that curve has a peak near the best height.

18. There may be small differences between acceleration values for the best chair heights in stronger subjects. A broader peak curve, or their peak strength will appear at different points in the range of motion at the hip and knee than others, meaning that optimal work surface height may have a wider range of acceptable heights, rather than a single, ideal height.

19. Fatigue of muscle groups over time may change the ideal heights when other muscle groups are substituted.

20. Pathologies may present that suggest supporting either lower or higher heights of the available furniture to emphasize a better position or range of motion that may be preferred for a particular joint complex. For example, an older subject with shoulder impingement syndromes or moderate to severe thoracic kyphosis may be advised not to use full forearm support at the higher end of the available range to avoid greater risk of injury.

21. Weaker subjects, or those with pathology or hip arthroplasty may show greater differences in the shape of the peak strength curves, or they may show bimodal curves. Sensitivity to those presentations will inform more detailed choices about workstation dimensions and chair adjustment.

22. Medical conditions like obesity or fused knee may require alternative chair designs and subsequent differences in seating strategies that may preclude adherence to the protocol described. Alternative medical needs should not defer the user from accommodating that need and preserve the general intent of the protocol to maintain best spinal posture.

23. Differences in shoe height may or may not change the torque curve, and varied shoe height may or may not require changes in the work surface height. Substantive objective data can inform that decision.

24. Fixed-height work surfaces may likely be preferred for cost or design requirements. Determination of the optimal height for a subject at fixed height surfaces may be better informed when data can be compared for the same or other subject's experience with adjustable height surfaces. Data collected for different work surface heights, including standing postures using subject anthropometry, chair height and leg strength data may inform either large-scale design strategies or individual workstation preferences.

25. Significant changes in subject girth at the hip and thigh may change the relationship of strongest seated height and floor-work surface height.

Static Method

In some embodiments, seat height can be selected based on force developed by the legs without significant motion of the chair. In these embodiments, the subject is asked to maintain a constant position, and to exert force of arms, legs, or torso against a table, elastic band, or to duplicate work movement. The force is measured using a transducer, such as a force plate, dynamometer, or magnitude of motion under conditions of uniform resistance from a cable tension or weighted arm movement, and the information from the transducer is recorded in memory of the processor. As with the dynamic method described above, a threshold can be selected below which the processor ignores a small or inconsequential measurement. These thresholds can be selected in the range of about 0.01 Newtons (N), 0.1N, 0.2N, 0.3N, 0.4N, 0.5N, or other desired threshold.

Once a series of measurements are stored in memory, the processor can then take an average of them. The seat position that provides the maximal forces with the smallest overall chair movement can be selected. However, in some situations, the desired seat position can be selected within about 5%, 10%, 15%, 20%, 30%, or other desired position.

Measurement of Hip-Spine Position

In embodiments of this invention, the posture of the lower back, preferably of the lumbar spine, can be assessed. In general, it is known that if the lower back (or spine) is properly aligned with the force of gravity, and if undue flexion or extension is avoided, then a person sitting at a workstation may experience less tension, pain and other symptoms of poor posture. Additionally, if the hips and lower back are in a good position, there can be fewer complications as other portions of the body tend to compensate. Thus, the legs, upper torso, arms, neck and head can be held in good posture, and can further avoid adverse symptoms.

To provide distinct observations of postures of the lower back, a new hip-spine device, such as a HIPINDEX™ tool can be used to show when the general forward-backward rotational position of the pelvis and low back are either in a favorable, or neutral position, or if the low back is in an extreme forward bending, or slumped posture. Use of a HIPINDEX™ indicator is shown in FIGS. 1 and 2. The indicator can be clipped, pinned or otherwise fastened at the side of the subject, to a belt or waistband that is snug around the bones of the pelvis (anterior and posterior superior iliac spines.

FIG. 1A depicts a drawing 100 of a person in an acceptable, partially reclined seated posture The chair pan and back angles are adjusted with the lumbar spine in neutral posture and the seat back reclined 15-20 degrees from vertical to support the lumbar spine with a reduced vertical load. A HIPINDEX™ tool is shown, with line 105 at the waist, line 110 perpendicular ("normal") to line 105. Position of thigh 115, and line 120 extending from the hip joint to the shoulder are depicted. Line 125 extends from the junction of lines 105 and 110 to the ear. Position the seat pan to forward or reclined angle (determined by prior postural observation, FIG. 13) to suppor neutral spine posture in the working posture (identified using the HIPINDEX™ and HIPPIC™ tools) then move the chair back to support the torso.

Figure 1B:
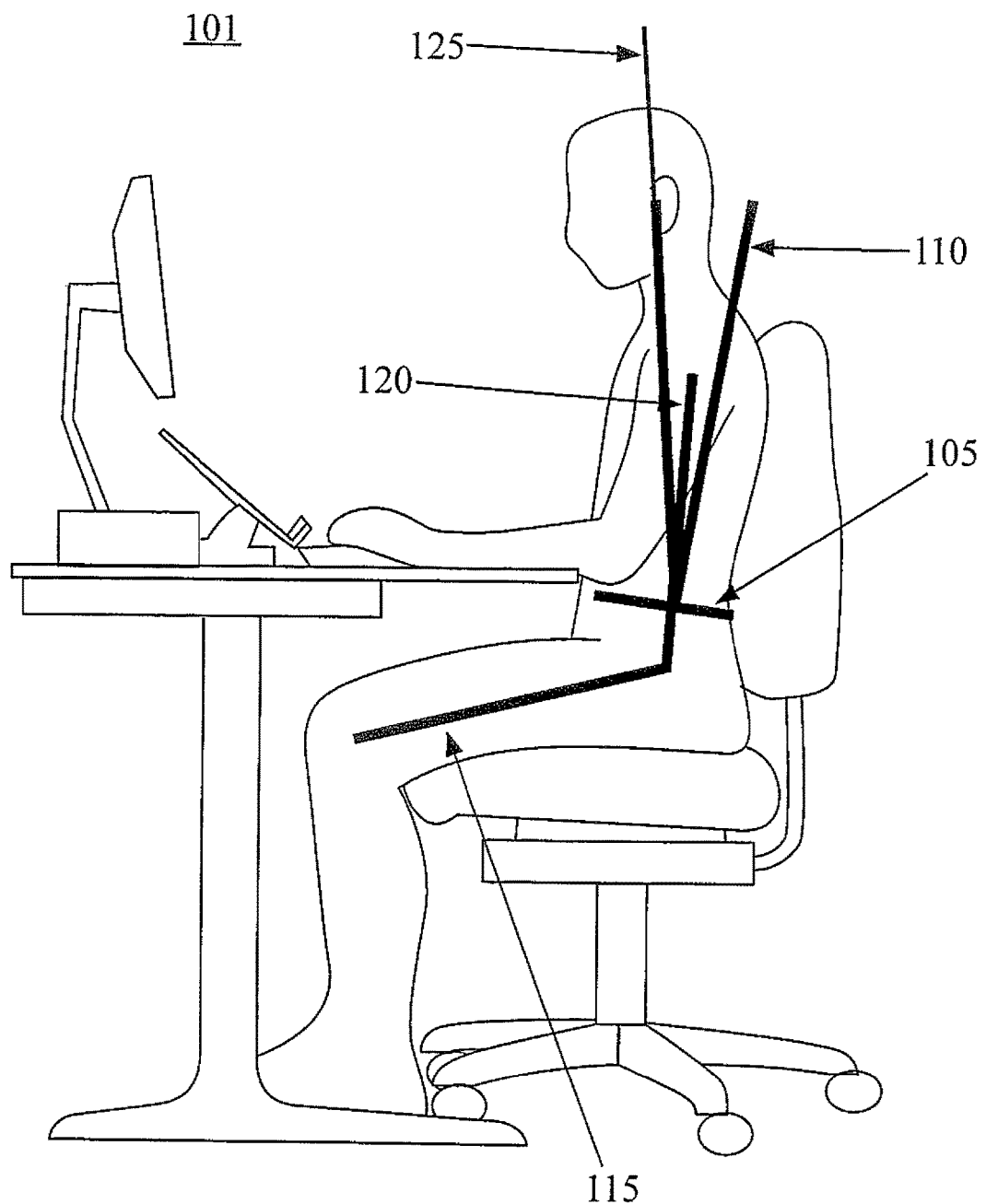
FIG. 1B depicts a drawing of a user seated at a workstation with a suitable erect posture.

FIG. 1B depicts a drawing 101 of a user seated at a workstation in a forward posture compared to the slightly reclined posture shown in FIG. 1A. A HIPINDEX™ tool shows the position of the user's waist 105 and line 110 normal to waist 105. Thigh position is shown by line 115, and the line from the hip joint to the shoulder is shown by line 120. Line 125 is shown also. As with the posture shown in FIG. 1A, lines 110 and 125 have a small angle between them, indicative of a desired spine neutral posture. Positions with less posterior pelvic rotation in the sagittal plane tilt are shown with smaller angles between lines 110 and 125, and preferably are less than 20 degrees.

Figure 2A:
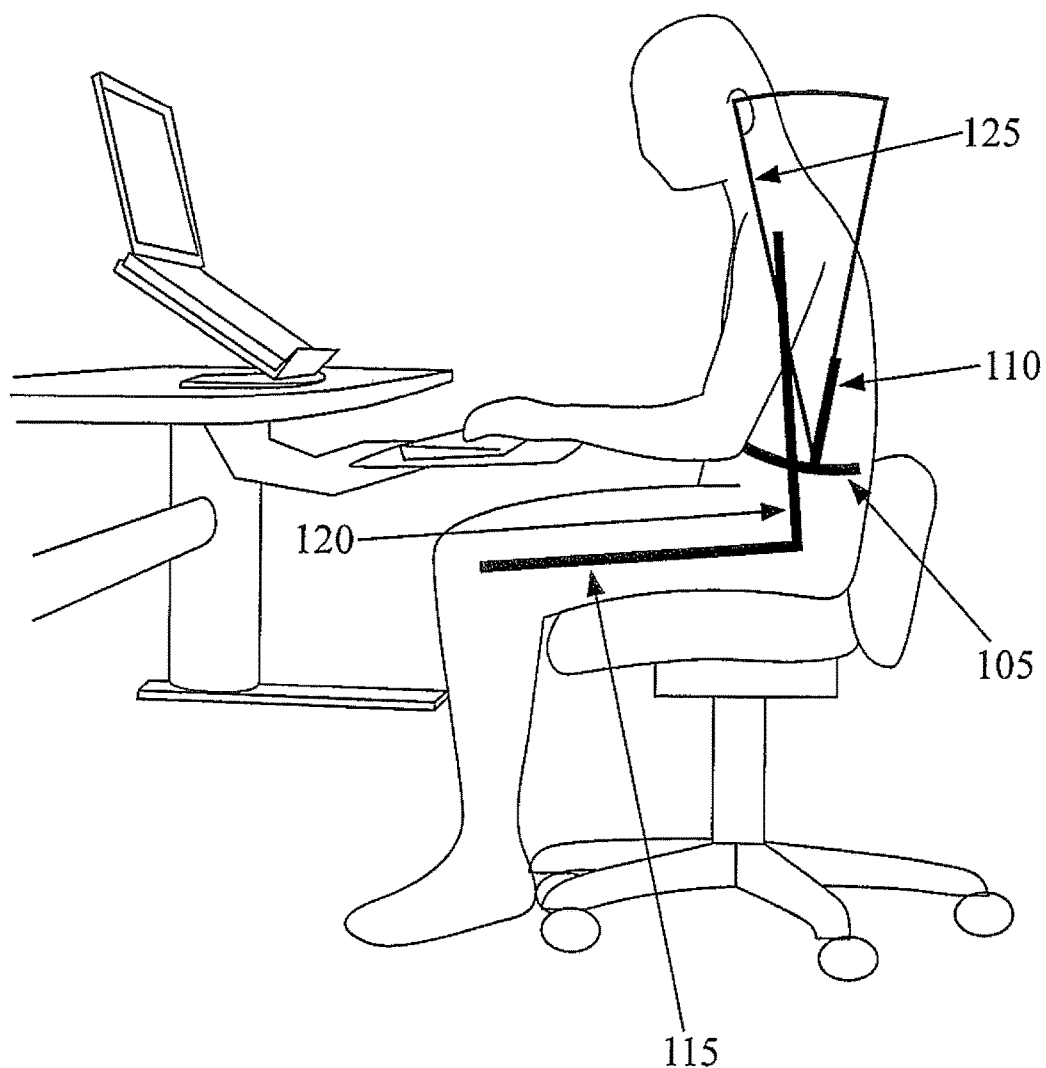
FIG. 2A depicts a drawing of a user seated at a workstation with a slumped posture that can produce adverse symptoms or dysfunction.

FIG. 2A depicts a drawing 200 of a user in a slumped position seated at a workstation with a HIPINDEX™ tool applied to the waist. The user's waist is shown as line 105. Line 110 is shown at a 90° angle to line 105. The thigh-torso angle between lines 115 and 120 is near the acceptable 90 degrees. In FIG. 2A, visual cues to the keyboard and the position of forearm support have drawn the torso forward. Line 125 is shown extending from the junction of lines 105 and 110 to the ear of the user. As can be seen from FIG. 2A, lines 110, 120 and 125 are not aligned. The substantial angle between lines 110 and 125 indicates a slumped posture.

Figure 2B:
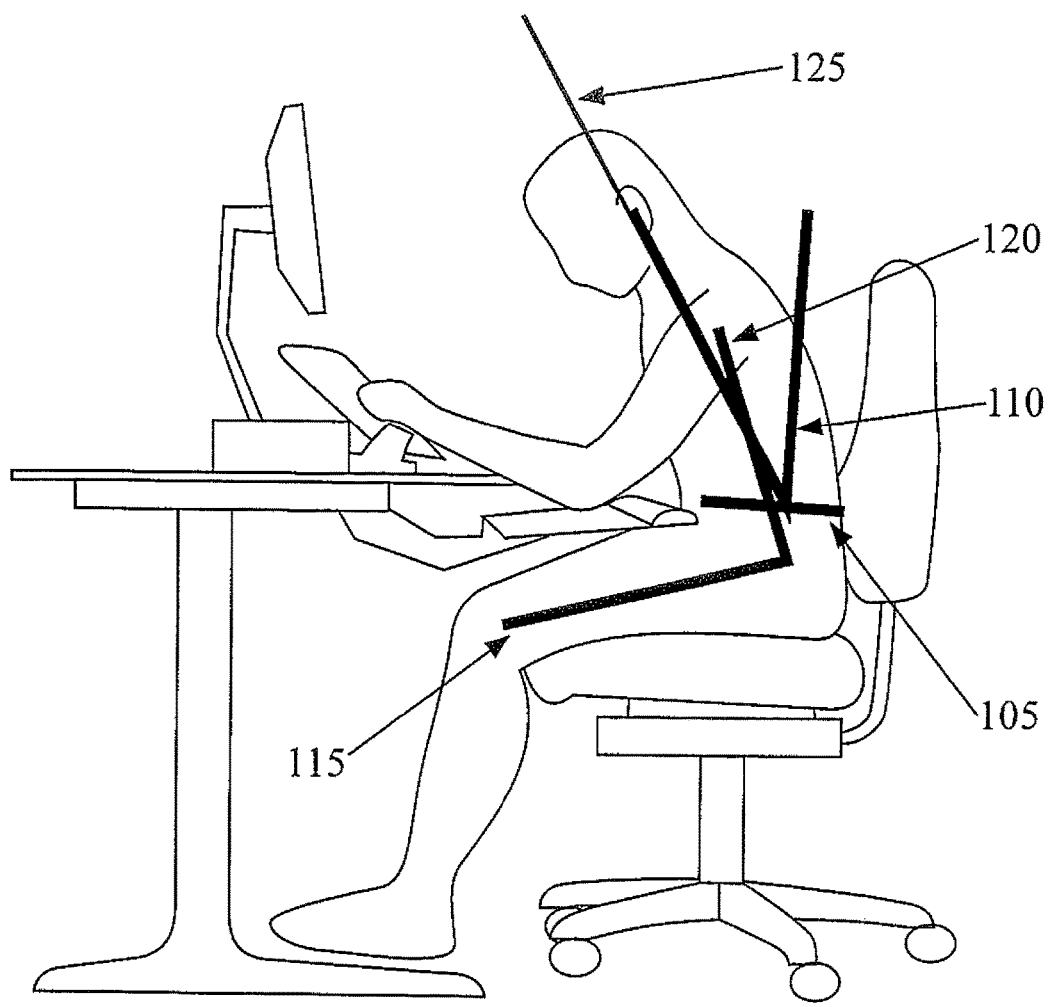
FIG. 2B depicts a drawing of a user seated at a workstation with a different type of slumped posture, leaning forward at a workstation.

FIG. 2B depicts a drawing 201 of a user in a forward posture using a chair with a level seat pan and back reclined 15-20 degrees. A HIPINDEX™ tool depicts waist 105 and the line 110 normal to 105. The thigh is shown at 115, and a line from the hip joint to the shoulder joint is shown as line 120. As with FIG. 2A, the line 110 is not aligned with lines 120 or 125, indicating a forward slumped posture. The pelvis is rotated backwards and the spine is drawn forward and into a slumping position. With the chair adjusted for reclined postures, such a forward position of the torso causes forward bending of the spine. The angle between lines 110 and 125 is shown to be greater than 20 degrees, indicating nearly full forward bending at the lumbar spine.

As can be seen in FIGS. 2A and 2B, the relatively large angles between lines 110 and 125 indicate a slumped posture, where the head is forward of line 110 more than shown in FIGS. 1A and 1B. About 30 degrees range of motion in the sagittal plane of the pelvis is possible, but there may be variations in range of 10-15 degrees. It can be useful to observe the range of motion for each subject. Supported postures in the first 10-15 degrees of forward pelvis rotation are preferred. Sustained postures in the last 25-30 degrees of backward pelvic rotation are not preferred.

Figure 11:
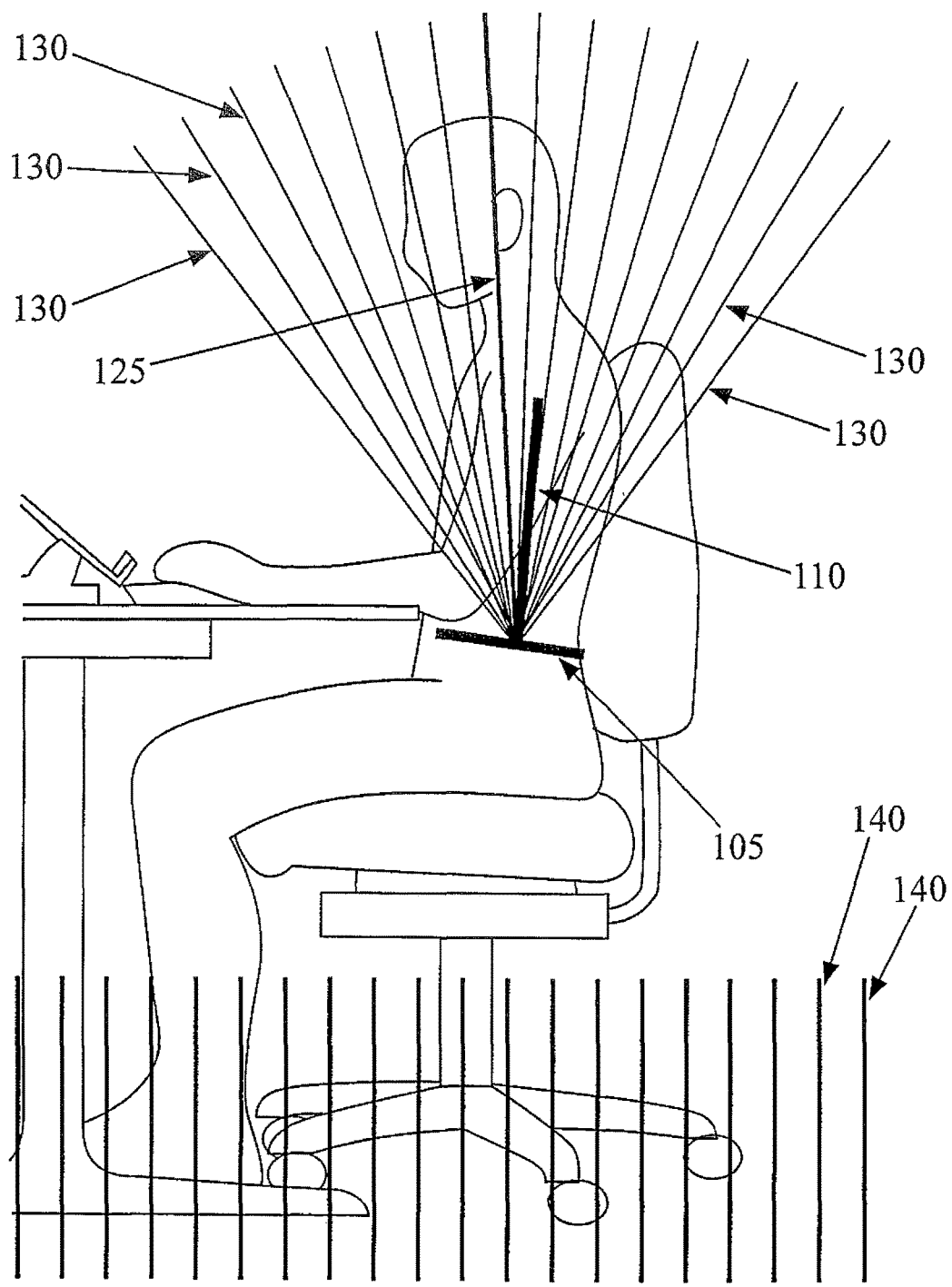
FIG. 11 depicts a drawing of an embodiment 1100 of this inverntion for analyzing seated spine posture. In this drawing, a user is shown in a desirable, spine neutral posture.
Figure 12:
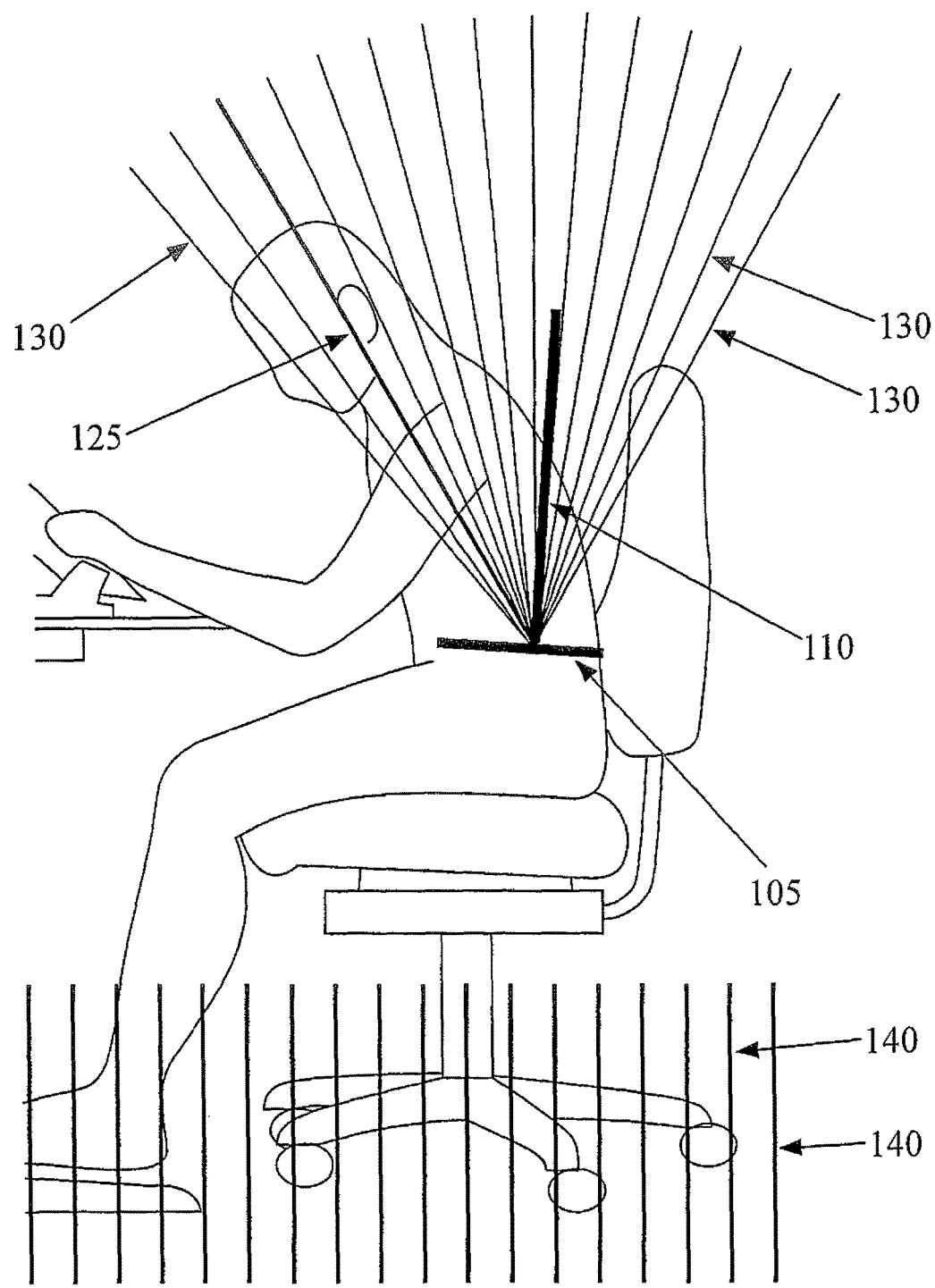
FIG. 12 depicts a drawing of an embodiment 1200 of this invention for analyzing seated spine posture. In this photograph, a user is shown in a forward slumpped posture.

Observation of forward/backward inclination of the torso or spinal postures can be made and calculated by use of photography and computer calculation, using, for example a HIPPIC™ tool (a trademark of Fitzsimmons & Associates, Oakland, Calif.). A calculation of the degree of torso forward/reclined inclination can be done with use of the HIPINDEX™ tool firmly positioned at the waist as described earlier in FIGS. 1 and 2 (see FIGS. 11 and 12), use of reference lines marked on a photographic viewfinder; the pertinent anatomical landmarks are identified and the photograph records the desired image. The software allows the angles to be identified on the photograph, and the processor calclulates the angle of spinal bending. FIG. 11 shows five degrees of forward inclination, with approximately 15 degrees of spinal bending, or near-neutral lumbar spine posture. FIG. 12 shows 20 degrees of forward inclination with nearly 30 degrees of spinal bending, nearly full forward slump posture. The amount of time in position for each of these tasks is then considered for the appropriate risk factor for spinal bending.

Neutral spine posture is identified with forward- to mid-forward pelvis rotation with lines 110 and 125 being within about 10-15 degrees of each other (FIGS. 1A and 1B), as distinct from slumped postures, identified by rearward pelvis rotation, in which lines 110 and 125 have an angle between them of greater than about 20 degrees (FIGS. 2A and 2B). A variety of work tasks may require either forward or reclined postures and the chair pan height and angle should support those tasks with a neutral spine posture. As used herein, the word "about" means within a range of +/−25% of the value.

In other aspects, it can be desirable to determine the relative percentage of time in forward tasks that require repeated or sustained forward reach to the work surfaces, visual cues to the work surfaces or the activity defined as "forward" and compare the percentage of time in reclined tasks to determine the direction of seat pan angle for those tasks, and make adjustments to meet those tasks with a neutral spine posture. For instance, a predominantly forward task that elicits slumped postures (FIG. 12) that is conducted for more than 10-15 minutes may be accommodated by tipping the seat pan forward to allow the pelvis to rotate forward and minimize lumbar spine bending.

In some embodiments it can be desirable to establish moderate rolling resistance with appropriate chair caster-floor surface agreement, i.e., carpet casters on carpet; soft casters or glides used on hard surface. Resistance to chair movement should allow the body to change position in the chair before the chair moves over floor.

Once seat height is chosen, based on observation of hip-spine neutral posture and measurement of leg strength, other portions of the workstation can be selected. Thus, lumbar support, desk height, chair arm position and height, headrest position, lighting positions, accessories (e.g., document holders), telephone, keyboard height, depth and angle if needed, screen location (e.g., location, angle, height), and proximity of reach to other items in a workstation can be adjusted to maintain a desired lower spine posture, and indirectly, the entire spine. If the girth or stature of a user causes adverse forearm support postures on the work surface or that degrade spinal postures, then chair/armrest position can be adjusted to provide relaxed shoulder movement, particularly during keyboard activities.

Devices for Analyzing Posture

Further aspects of this invention includes accelerometer-based devices having at least one computer processor, memory, computer implemented programming instructions, and display features. Processors of such devices can be programmed to detect and quantify acceleration and deceleration, and from this information, produce graphical displays of acceleration versus chair height and/or acceleration versus seat pan angle.

A processor can include instructions to perform the following steps:

i. accepting data from accelerometers providing gravity data for three dimensions of motion, an "X" dimension, a "Y" dimension, and optionally, a "Z" dimension, each of said dimensions being perpendicular to each of the other dimensions, said data being "gravX", "gravy", and "gravZ", respectively, each expressed as the effective gravitational acceleration in each of said dimensions;

ii. sampling said gravity data at a frequency of about 1 time per second to about 40 times per second, and storing said data in said memory;

iii. updating said gravX, gravy and gravZ values where said updated values are calculated according to the following formulas:

$$gravX = alpha*gravX + (1-alpha)*ev.x;$$

$$gravY = alpha*gravY + (1-alpha)*ev.y;$$

$$gravZ = alpha*gravZ + (1-alpha)*ev.z;$$

where alpha is a time interval for a low pass filter, ev.x, ev.y, and ev.z are new gravity data in the X, Y, and Z dimensions respectively. Generally, alpha is between zero (0) and one (1). Preferably, alpha is between 0.1 and 0.9, more preferably between 0.2 and 0.8, still more preferably between 0.3 and 0.7, even more preferably between 0.4 ad 0.6, and yet more preferably 0.5;

iv. calculate acceleration by removing the gravity contribution using a high-pass filter according to the following formula:

$$accX = ev.x - gravX;$$

$$accY = ev.y - gravY;$$

$$accZ = ev.z - gravZ,$$

where accZ, accY, and accZ are accelerations in the X, Y, and Z dimensions, respectively; and v. calculating for each time point, total linear acceleration ("A") according to the formula:

$$A = (accX^2 + accY^2 + accZ^2)^{1/2}; \text{ and}$$

vi. storing said values of A in a memory of the device.

A processor can also be programmed to display acceleration values versus chair height and/or acceleration values versus chair pan angle.

Monitoring of Motion During Work

Using methods and devices disclosed herein, once a subject is properly seated at a workstation, with neutral spine posture (at or near the midrange of normal spinal curvature), periodic relatively small adjustments of posture of the subject can be recorded. The periodic adjustments can help maintain proper tone of postural muscles, can improve venous return from the muscles, relieve stress on joints, and create an overall improved experience.

In contrast, we have found that subjects seated with either a "too-forward" (too much flexion or "slumped") posture, or a "too-reclined" (too much extension) posture, or a laterally tilted (left or rights) posture, tend to remain in a relatively fixed posture, with few periodic adjustments. Thus, the tone of postural muscles can be lessened, in some cases can lead to muscle cramping and pain, thereby exacerbating poor posture. Additionally, venous return can be compromised, and joints may become painful or stiff without such small, periodic motions.

Accelerometer-based devices and methods can be programmed to continuously record such relatively small periodic motions, and when displayed, can provide the user (subject) with feedback useful for maintaining ergonomically efficient postures.

Thus, in some embodiments, a mobile computer device can be programmed to monitor accelerations in an ongoing fashion, to record such periodic movements, and if desired, to display those motions to the user. To monitor relatively small motions, the programming instructions can be modified to display ongoing movements, and not simply produce average movements. To accomplish these aims, parameters of the low-pass and/or high-pass filters can be adjusted to produce clear, accurate indications of motion without either over-damping or under-damping. Over-damping may reflect a "low gain" of the system in which small motions may be missed and not recorded, and under-damping can produce too much noise in the signal, making observations of small motions difficult or impossible.

Prior Strategies

Thus, this invention provides new methods and devices to improve ergonomics for persons engaged in seated workstation activities. These new methods and systems are improvements over those of the prior art.

Most current ergonomic guidelines suggest that only one reclined sitting posture is preferred, and that alternative postures may include a break from that sitting posture, either to stand, or to walk briefly. ANSI and NIOSH use thigh-torso angles similar to Dainoff that determine optimal chair posture, but that strategy does not identify the rotation of the pelvis to the torso, which is a primary determinant of lumbar spine position. Additionally, lumbar disc pressures have been measured in several postures (Nachemson 1964, 1974) and that information has influenced preferred seating positions with: 1) the lumbar spine in neutral posture, with the best natural curves, and 2) the seat back reclined 15-20 degrees from vertical to support the lumbar spine with the least vertical load (FIG. 1). Others (HFES, 2012) suggest that increasing chair back recline up to 30 degrees is preferred. Dainoff (1986) proposed a system currently in use that identifies the body's anatomic landmarks using the angle of the lines between the torso (hip to shoulder) and the thigh (knee-hip) to be a preferred angle approximately 90-105 degrees in upright posture. Height measures for the knee, elbow and eye height are taken to determine the relative workstation dimensions for chair adjustment, monitor height, and work surface or keyboard tray height. However, the above prior methods have not considered the roles of pelvis position in seated posture.

Acceptable thigh-torso angles can mask slumped posture with nearly full forward bending of the lumbar spine (FIGS. 2A and 2B).

U.S. Pat. No. 8,195,475 describes a strategy based on the idea that the seated posture should conform to specific angles at the thigh-torso and knee, rather than functional strength postures with the spine in neutral position, independent of specific angle measures at one instance of the leg position. Spinal collapse or slumping is a problem to be solved, but according to the '475 patent, the primary solution is to add lumbar support to the chair, rather than identifying the leg strength and pelvis position.

Prior designs presume some combination of the following: a) the user will determine their best posture, and then workstation will then automatically adapt to that posture, or b) the designs will either accommodate, conform to, influence or otherwise determine the user's proper chair and workstation adjustments for that user, based on stature, movement or task, including breaks and movements that may be programmed for the system or user.

Prior designs do not provide guidelines to provide optimal seated postures based on neutral spine position or the musculature that supports the spine, nor do they suggest any adaptation or adjustment for the many chairs and workstations currently in use.

EXAMPLES

This invention is described with reference to specific embodiments thereof. Other features of this invention can be appreciated with reference to the Examples. It can be appreciated that these are only examples to illustrate features of this invention. Other embodiments can be created by those of skill in the art without undue experimentation and with a reasonable likelihood of success. All such variations are considered part of this invention.

Example 1: Attachment of Accelerometer Device to a Chair

Figure 3:
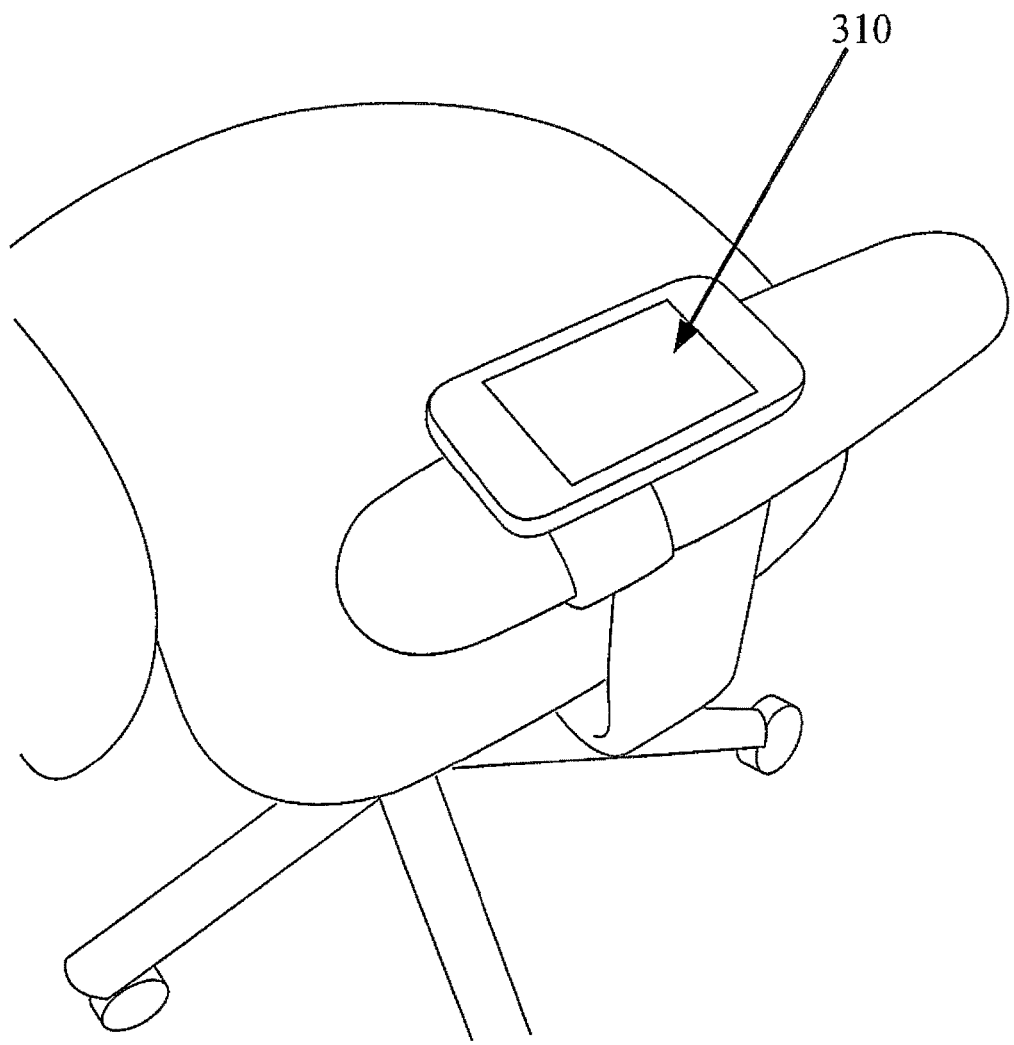
FIG. 3 depicts a drawing of an embodiment of this invention in which an accelerometer/processor/phone device is attached to the chair arm with Velcro® strap to provide stable, temporary support on the chair for data collection, recording and processing.

FIG. 3 depicts a drawing 300 of an embodiment of this invention in which an accelerometer/processor/phone device 310 is attached to the chair arm with a strap to provide stable, temporary support on the chair for data collection, recording and processing.

Figure 4:
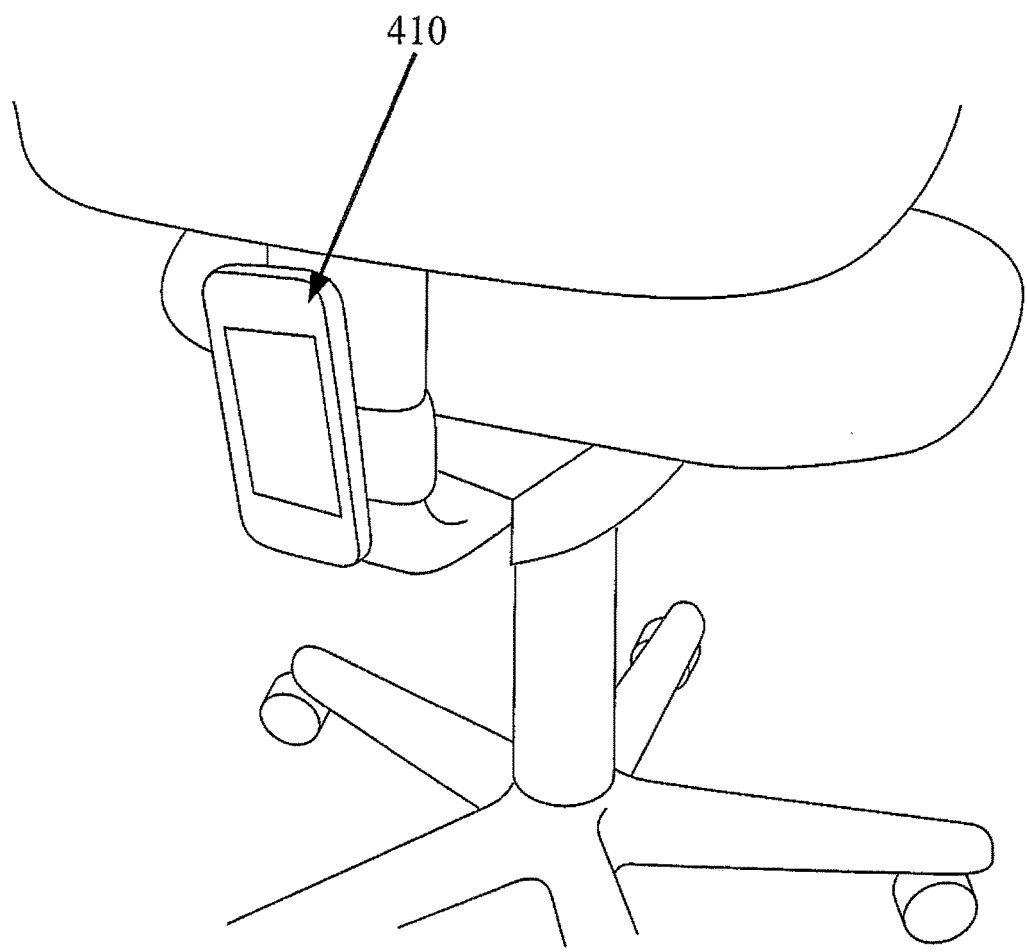
FIG. 4 depicts a drawing 400 of an embodiment of this invention in which an accelerometer/processor/phone device attached to the chair back support with Velcro strap to provide stable, temporary support on the chair for data collection, recording and processing.

FIG. 4 depicts a drawing of an embodiment 400 of this invention in which an accelerometer/processor/phone device 410 attached to the chair back support with a Velcro® strap to provide stable, temporary support on the chair for data collection, recording and processing.

Figure 5:
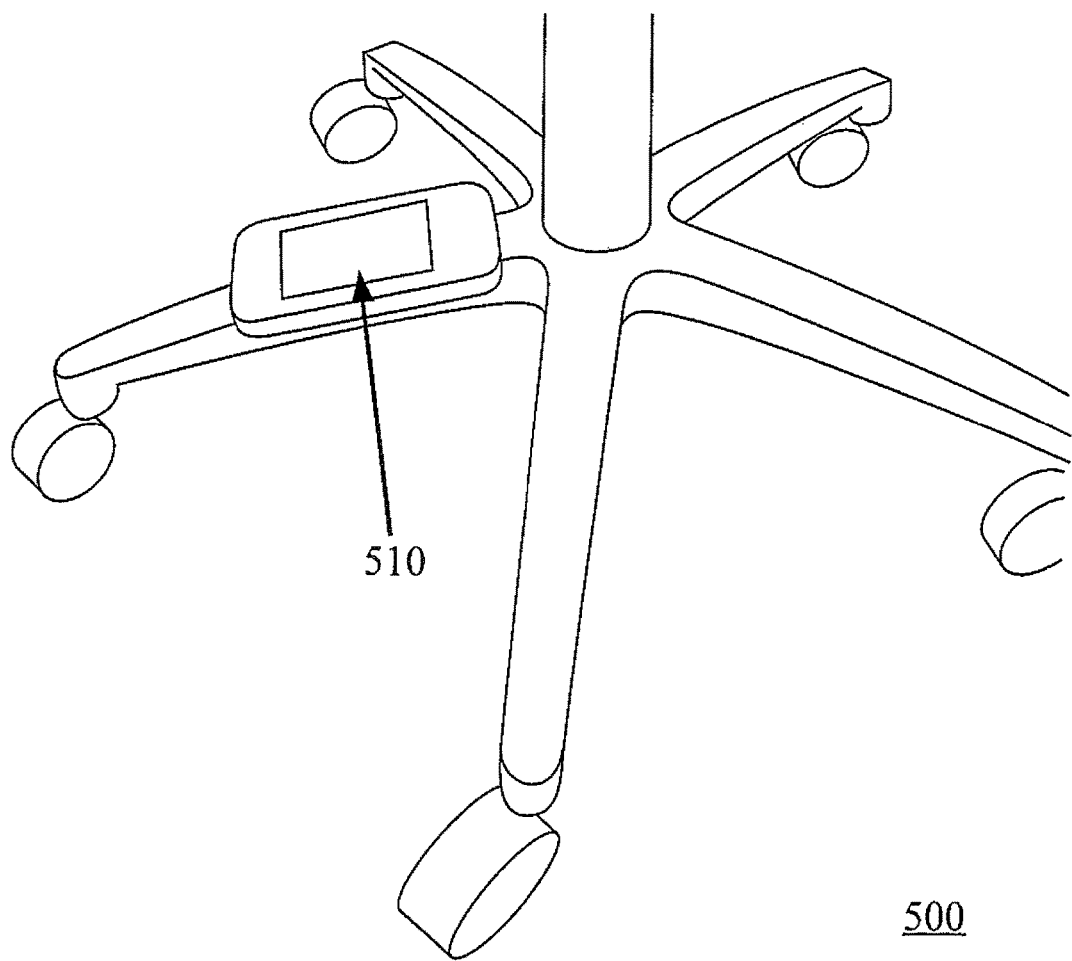
FIG. 5 depicts a drawing of an embodiment of this invention in which an accelerometer/processor/phone device attached to a chair base with Velcro tape to provide stable, temporary support on the chair for data collection, recording and processing.

FIG. 5 depicts a drawing 500 of an embodiment of this invention in which an accelerometer/processor/phone device 510 attached to a chair base with Velcro® tape to provide stable, temporary support on the chair for data collection, recording and processing.

Figure 6:
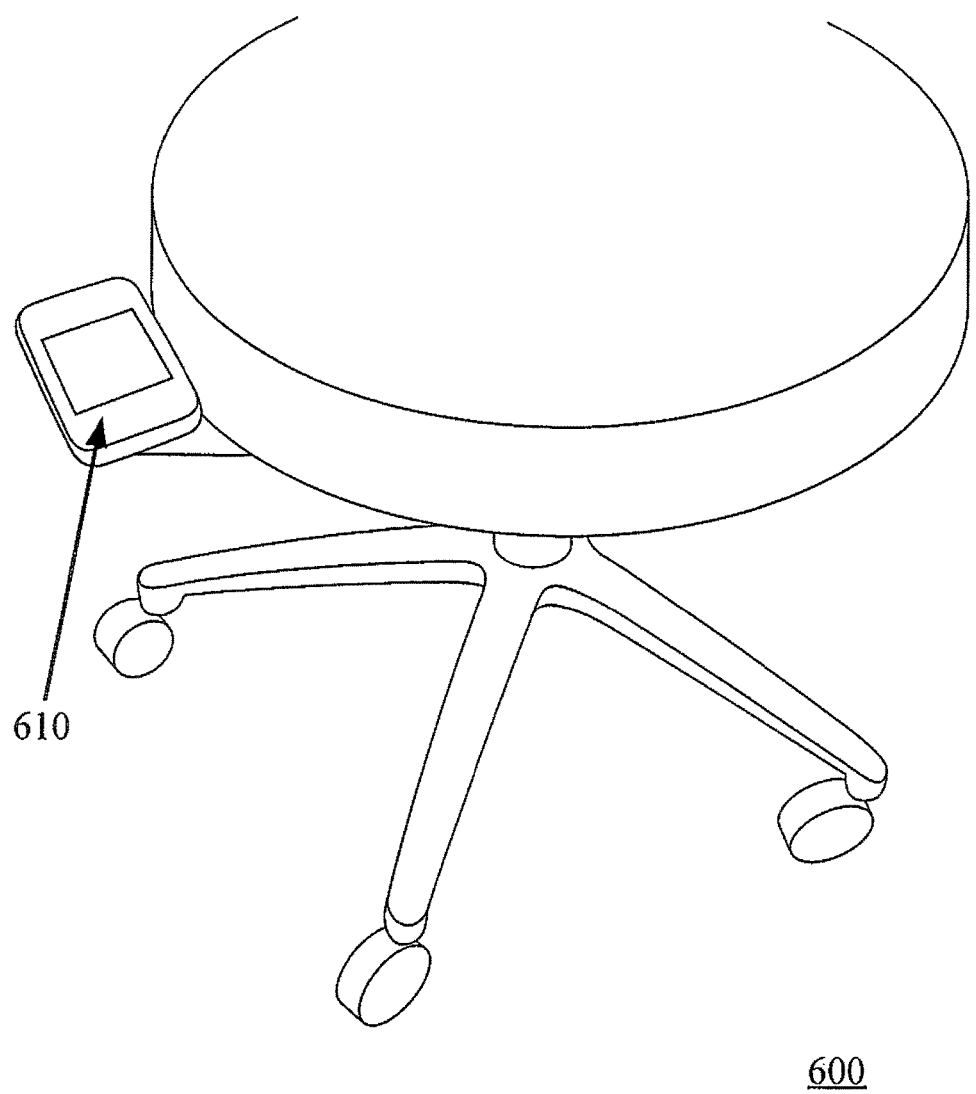
FIG. 6 depicts a drawing of an embodiment of this invention in which an accelerometer/processor/phone device attached to the testing stool platform with Velcro backing to provide stable support on the stool for data collection, recording and processing.

FIG. 6 depicts a drawing of an embodiment 600 of this invention in which an accelerometer/processor/phone device 610 attached to the testing stool platform with Velcro® backing to provide stable support on the stool for data collection, recording and processing.

Example 2: Measuring Hip-Spine Position

Figure 7:
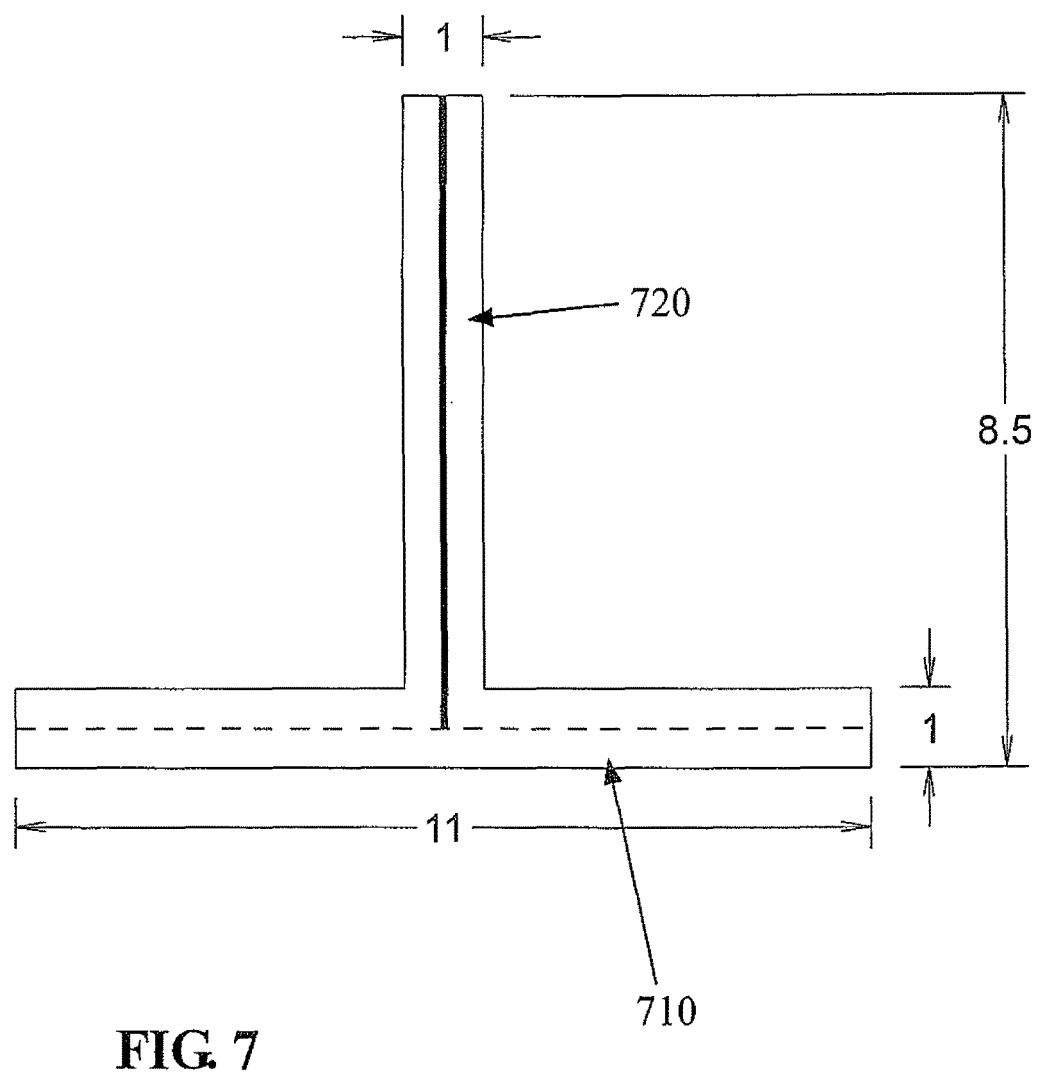
FIG. 7 depicts a drawing of an embodiment of this invention, a Hipindnex™ tool that can be useful for determining lower spinal position.

FIG. 7 depicts an embodiment of this invention 700, in which hip-spine position is evaluated. Hip-spine position can be evaluated using a HIPINDEX™ tool, which can be made from an appliqué of paper or light plastic. The tool is positioned to fit snugly at the waistband 710 and generally shows the range of sagittal plane rotation of the pelvis as a field indicator of optimal lumbar spine position. A line 720 is normal to the waist line 710.

A subject can reliably choose the optimal chair height (correlation coefficient>0.94) when properly challenged without external measurement tools, but chair height and concurrent work surface height may change over time with anthropometric changes (weight gain or loss) or encounter short-term changes evident by footwear, task, or chair design.

Objective measures can be determined with use of a device containing an an accelerometer, mounted on the chair, using either a manual or automated data collection process, and a processing unit using proprietary software and algorithm to calculate acceleration values. A strategy is provided to determine when to use or delete an articulated keyboard tray/arm. A strategy is provided to determine the forward/reclined bias of the torso for a work task, which determines critical chair adjustments.

Determining Spine-Neutral Postures

To determine spine-neutral postures, one can perform one or more of the following steps.
1. Instruct the subject in postural cues and the seating measures protocol. The subject is provided a visual image (movie, series of photographs or they are asked to watch a physical demonstration) of a body moving from slumped sitting to upright posture; the subject is given verbal cues including one or more of: "sit up tall, with your feet on the floor; as though you were looking over a fence;" "move your shoulders down and back," "then gently tuck the chin back and down to feel a pull at the back of the head;" "take a breath through the abdomen," and "breathe out with the torso in the upright position." The subject is also given physical cues: the instructor can gently guide the back of the waist forward to encourage forward rotation of the pelvis; gently guide the shoulders back and down; gently lift the head using light pressure at the upper neck.
2. Provide the subject with visual, verbal and physical cues to sit upright in neutral spine posture, as in section 1 immediately above.
3. Inform the subject that several chair heights will be tested for their ease of movement using standard or regular shoe heights.
4. Demonstrate movement of the chair front-back, side-side, and/or diagonal directions, with upright body orientation and stable foot position. The movement can be demonstrated with a video film clip or series of photographs that show firm foot position on the floor with the feet at shoulder width, and the subject moving the chair forward and backward; then side-side with the chair at one height. The movement can also be demonstrated by the instructor or by a designated model to show the movement.
5. Ask the subject to repeat the movements using a chair with reasonable chair fit and level pan. Reasonable chair fit consists of a seat pan size that fully supports the leg and hip, and allows 1-3 inches space from the front of the seat pan to the back of the knee to allow leg movement without restricting movement or causing pressure at the back of the knee.

Example 3: Strategy for Using Leg Strength for Workstation Postures

Figure 8A:
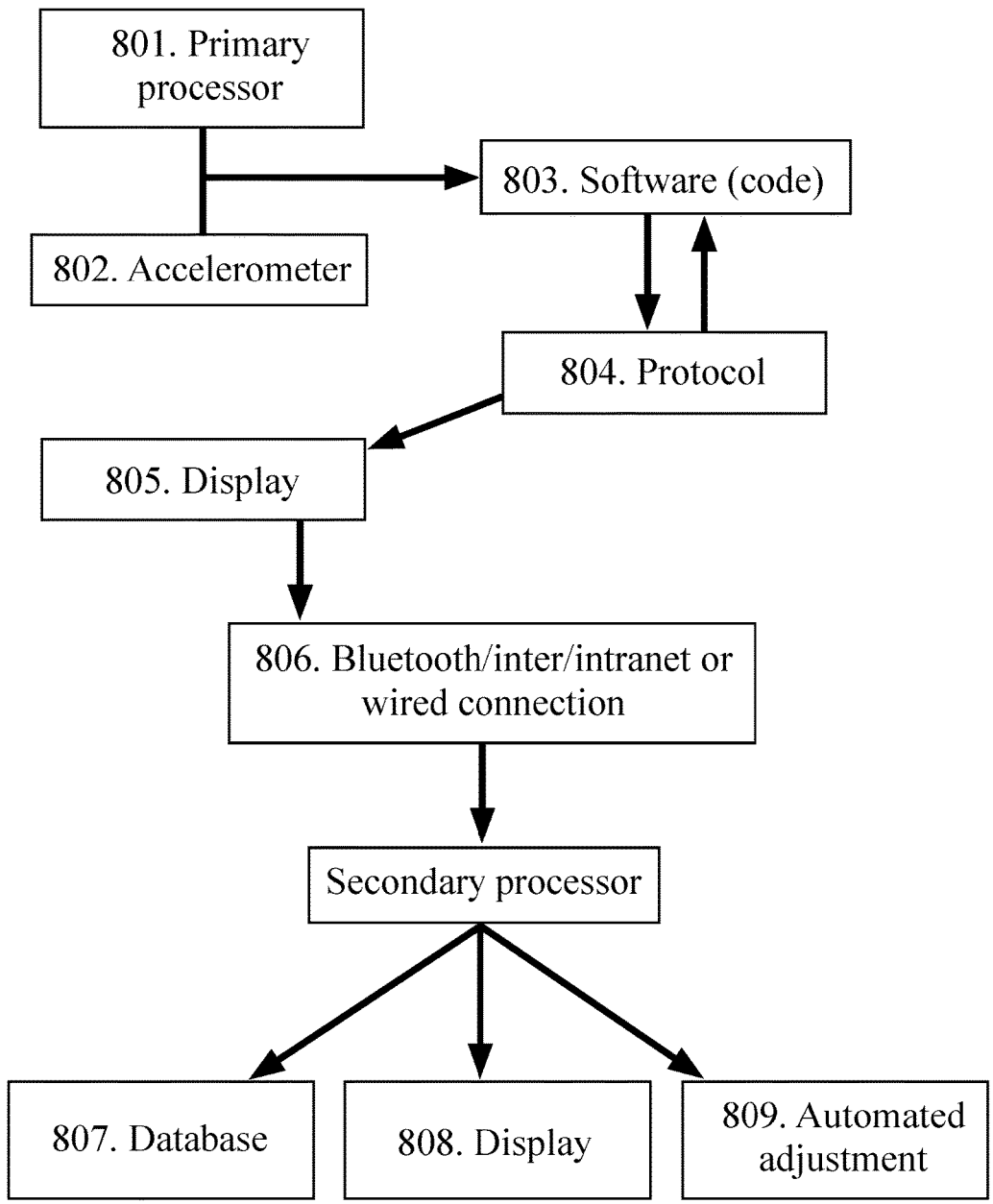
FIG. 8A depicts a flow chart of processes according to an embodiment of this invention that uses leg strength to determine seated work postures, chair adjustment and workstation configuration.

FIG. 8A depicts a schematic diagram 800 of an embodiment of a method for collecting and processing acceleration data from a chair-mounted device. Data from Accelerometer(s) 802 is sent to the Primary Processor 801 located in the phone or other device is a direct and simple embodiment. That data is used for storage and data processing by the installed Software 803 for data analysis. Protocol 804 is used to select and manage statistical and mathematical data algorithms can be adapted to several protocols determined by the user or the software. Protocol 804 may include: linear: calculation for total maximum acceleration, sum of squares, linear regression, weighted averages; characterize and compare linear performance at several pan heights; static/isometric: calculation for least acceleration; similar protocol to determine least movement during resisted challenge; dynamic: isolated calculations for defined vectors during dynamic movement; least deviation from proscribed and/or resisted chair movement, i.e., linear fore/aft, side-side diagonal movement; least deviation from proscribed and/or resisted arm or torso challenges and movement.

Steps depicted in FIG. 8A can be used to characterize movements with variable or freely moving pan height or angles, and those results are presented either as Display 805 on the device, or an alternate visual display, with audio components considered to identify specific points of range. The connection from processor to display can also be remote 806 (Bluetooth™, internet, radio frequency) or wired connection, and a secondary processor or server can serve as a secondary Processor for data management, storage or display and processing. Those data may include several categories of client profile, demographic, anthropometry, work location and type, medical history, workstation dimensions, equipment, process and chair fit, features and design, photography, audio recording, particulars of environment or equipment, or prior comparisons. Although a simple embodiment can include a visual display of the processed and raw acceleration data, alternate data categories can be displayed if pertinent: digital or analog display, prior acceleration data, best recorded height; supporting stimuli can be used for high and low readings, like audio tone or light display.

As depicted in FIG. 8A, Database 807 (data management and process) can include client profile information, including age, tasks, chair type, shoe weight, floor surface, caster design, upholstery, pan shape, page size, pan angle, work surface, dimensions, and database support for selected administrative outcomes, and processes related to the ergonomic process.

Also as depicted in FIG. 8A, Display 808 can include data pertinent to other aspects of ergonomic assessment. These may include indicators (e.g., visual lighting and readout, analog meters, auditory tones or sound or pitch related, vibrations of seat or arms or work surface, or in indication of unattached element), angle measures, light and sound intensity, templates for recording ergonomic data and supporting educational materials, available products and processes, vendor lists, and data links.

Additionally, FIG. 8A depicts Automated Adjustment 809, which can be effected by the data elicited from the chair height and workstation adjustments, so that where possible, a motor controller or servo-controller to adjusts a work surface with individual IP addresses can compare chair and work surface (e.g., table or keyboard) heights and movements to determine desirable height and movement patterns for different users, with work tasks and time of day to minimize awkward, sustained postures and maximize productivity.

Alternatively, the raw data from Primary Processor 801 and Accelerometer(s) 802 can be sent to an alternate location via the primary processor in the device via step 806 using remote (Bluetooth™, internet, radio frequency) or wired connection, and a server or other device can serve as Secondary Processor for data management, storage or display and processing, without use of a dedicated telephone device.

Figure 8B:
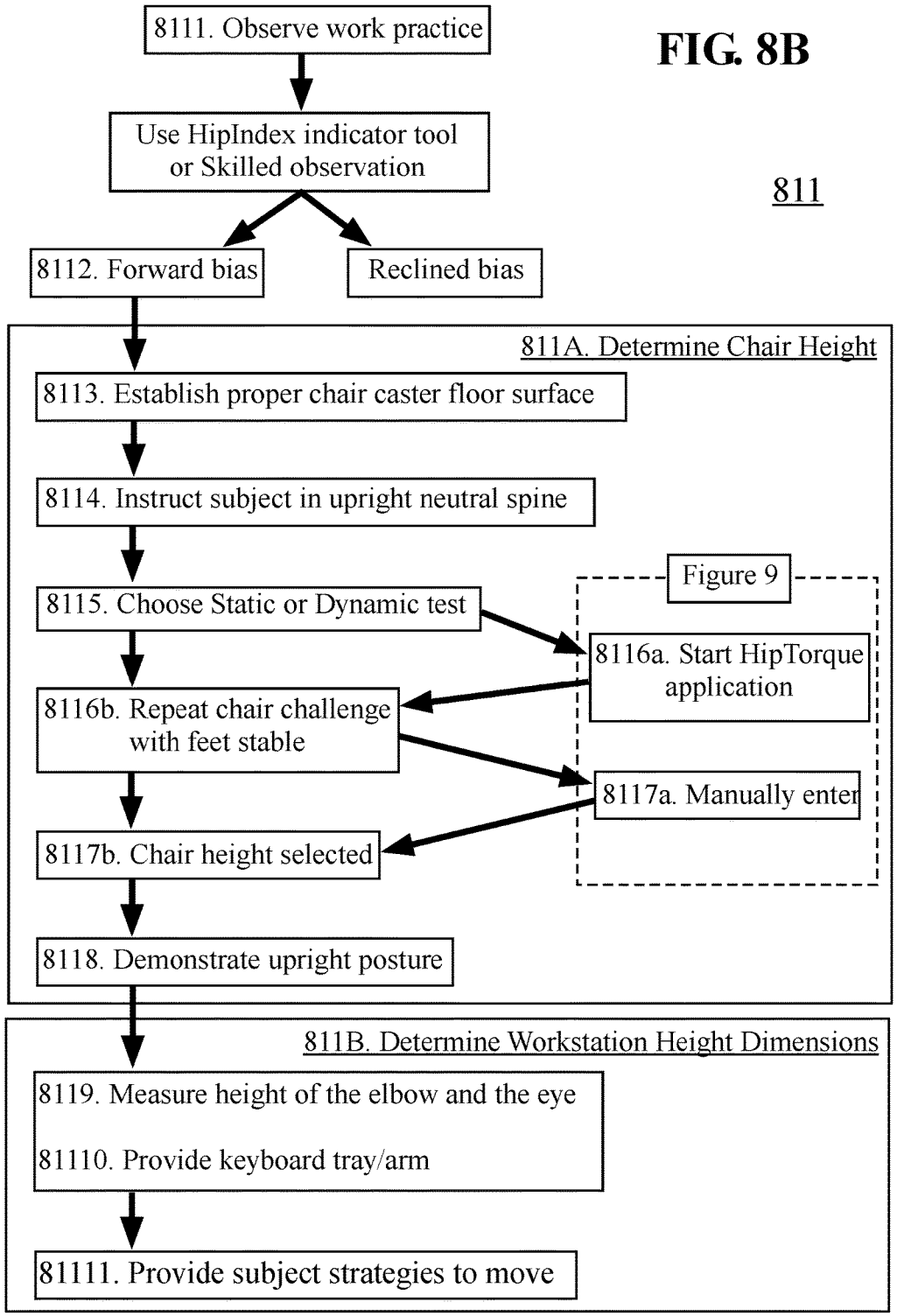
FIG. 8B depicts a flow chart of processes according to an embodiment of this invention to determine proper workstation height dimensions.

FIG. 8B depicts a schematic diagram 811 for a strategy to use leg strength to determine optimal seated work postures and workstation configurations. As depicted in FIG. 8B, in Step 8111, observe work practice to determine keyboard use and work bias with neutral spine posture. Use HIPINDIX™ indicator tool to characterize spine posture, or, skilled observation of neutral spine posture without use of HIPINDEX™ indicator. For Reclined bias work, no change from existing standard is needed. In Step 8112, analyze Forward Bias and Reclined bias work. Use leg stabilization protocol for chair height.

As depicted in FIG. 8B, in 811A, Determine Chair Height, with reference to Steps 8113-8118. In Step 8113, establish proper chair caster-floor surface relationship for resisted chair movement. In Step 8114, instruct subject in upright neutral spine postures using level seat pan. In Step 8115, choose static or dynamic test (arm or chair movement) with feet stable on floor.

As depicted in FIG. 8B, in Step 8116a, Start HIP-TORQUE™ application; manually enter ID data, testing details as needed, and initial chair height. In step 8116b, instruct subject to change chair height and repeat step 8116a with feet stable at several chair heights from too high to too low. In Step 8117a, enter each measured chair pan height into the application, run HIPTORQUE™ trail at each height—record or file the acceleration data for that height, repeat testing sequence for every chair height tested, objective test data can be used to refine selection when either the subject or the conditions are confounded.

Also as depicted in FIG. 8B, in Step 8117b, chair height is selected based on maximum leg torque data obtained in steps 8116a and 8116b. Once the data is collected, analyze to confirm best height. In Step 8118, demonstrate upright posture for work tasks let seat pan float or provide 5-15 degrees of forward tilt in the seat pan angle and retest height.

Also, as shown in FIG. 8B, 811B: Determine Workstation Height Dimensions with reference to Steps 8119-81111. In Step 8119, measure the height of elbow and eye to predict heights of work surface and monitor. In Step 81110, provide an adjustable keyboard tray/arm if intended for prolonged or sustained use (75-100 minutes). In Step 81111, provide subject strategies to move between forward, reclined, and neutral postures. There are now two strategies to sit with neutral spine posture that are based on the nature of the work bias: upright posture with leg support and forward tilt of the seat pan (0 to positive 15 degrees) for forward work (FIG. 1B), and upright posture with rearward tilt of the seat pan (0 to negative 5 degrees) and lumbar support for reclined work (FIG. 1A).

The user is instructed to identify those tasks by the forward and reclined postures the work may require, and adapt the seated posture to support a neutral spine position. For instance, time spent solely on the phone or with an interview may be identified as a reclined task, and the chair will be adjusted into a reclined posture. Time spent with mixed tasks on the work surface, combined with short entries to the computer keyboard is identified as a forward task, and the chair will be adjusted to provide support for the neutral spine in a more forward inclination. The alternation of postures between forward and reclined tasks presumes use of an ergonomic chair with suitable adjustment between forward and reclined postures and the reasonable choice of the user. The choice to alternate between forward and reclined postures can depend upon the reasonable differences in work tasks, and can generally limit sustained sitting in either posture to less than one-half hour, interrupted by a brief opportunity to stand and/or walk.

Predictions for work surface height can be made based on the measures of the height of the elbow with the spine in near-neutral postures, the hands clasped in front and the arms relaxed at the sides, and the body inclined in a working posture. The initial prediction for surface height is one inch above the resting elbow height when the shoulders are relaxed and the hands are clasped in front of the body. Variations on that height may include individuals with larger forward girth of the abdomen, which will predict a higher work surface, or require forearm support on the chair armrest to support the shoulder, and the nature of the task, which may require higher arm support or visual attention, or the assembly of products that are above the work surface, and the height of the product may require alteration of the surface to maintain the shoulder in neutral postures.

A prediction for monitor height is the location of the monitor's top line at the height of the eye, anticipating that the highest regular visual angle to the monitor will not be above level, and preserve the neutral postures from the lower spine to the upper neck. Use of eyewear, including multifocal lenses may require lowering the monitor height to preserve neutral spinal postures. Multiple monitor arrays or the use of taller monitors may require alternative strategies to maintain neutral spinal postures, like reclined seating or monitor position below the work surface. The goal of these ergonomic strategies is to maintain resting support of the spine in neutral postures during the intended work task.

Figure 8C:
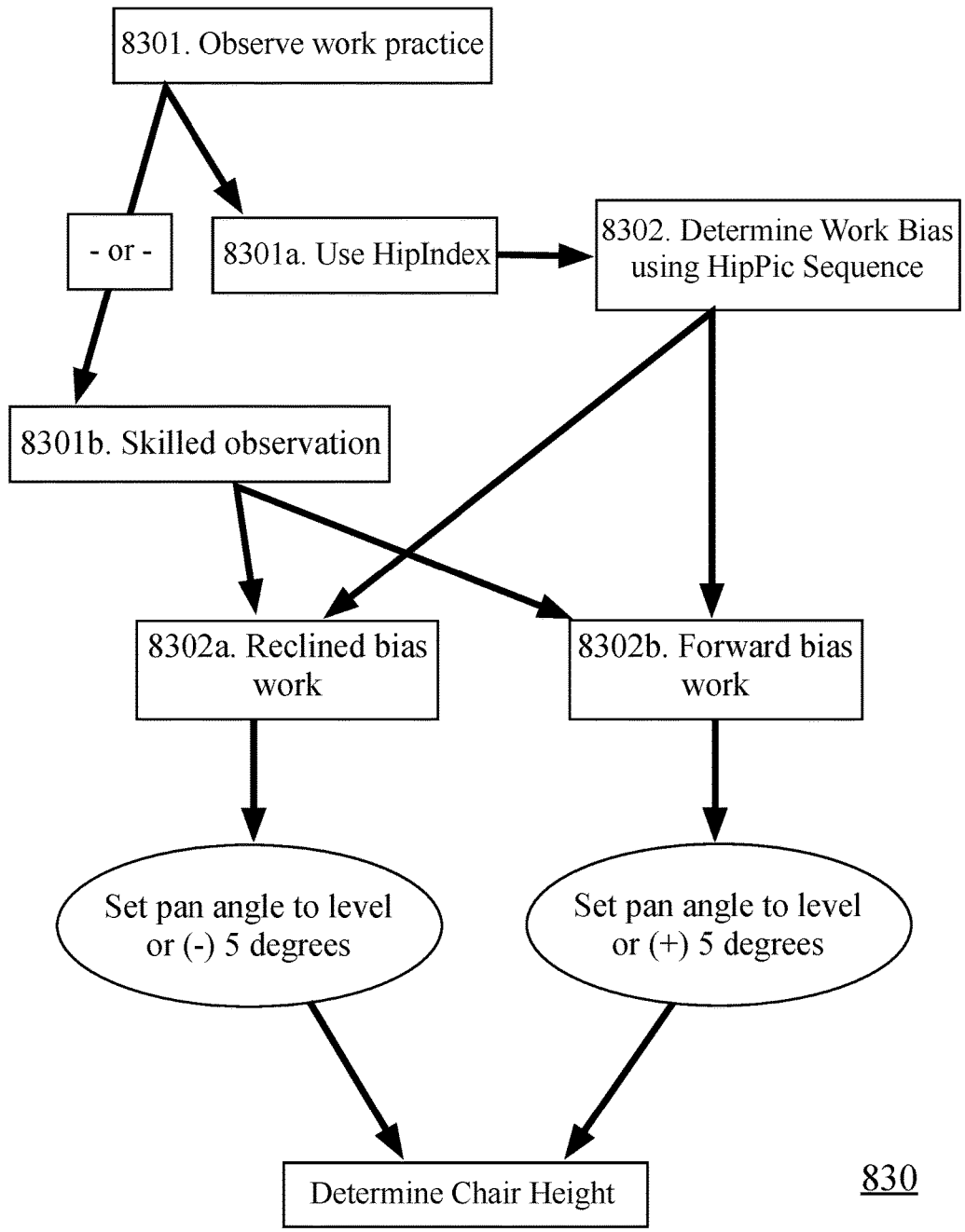
FIG. 8C depicts a flow chart of processes according to an embodiment of this invention to determine chair height.

FIG. 8C depicts embodiment 830 showing Steps 8301-8302 of FIG. 8B expanded to show how to differentiate between forward and reclined bias work prior to determining chair height. As shown in FIG. 8C, Step 8301, observe work practice to understand the nature of the tasks required: use of arm support, shoulder reach and visual targets required for repeated or sustained work as a discrete task, or a mix of similar tasks that combine for more than 5-10 minutes. In Step 8301a, use HIPINDEX™ tool, or in Step 8301b, a skilled observer.

FIG. 8C, Step 8302, Determine Work Bias using IPP-PIC™ tool. In Step 8302a shows Reclined Bias work using reclined chair adjustment. Here the chair is positioned with a level or slightly reclined seat pan (0 degrees to negative 5 degrees) and the subject is observed during representative work.

FIG. 8C, Step 8302b shows calculations for Forward Bias work using reclined chair adjustment. Here the chair is positioned with a level or slightly forward positioned seat pan (0 degrees to positive 5 degrees) and the subject is observed during representative work. Based on Steps 8302a and 8302b, Determine Chair Height.

Figure 9:
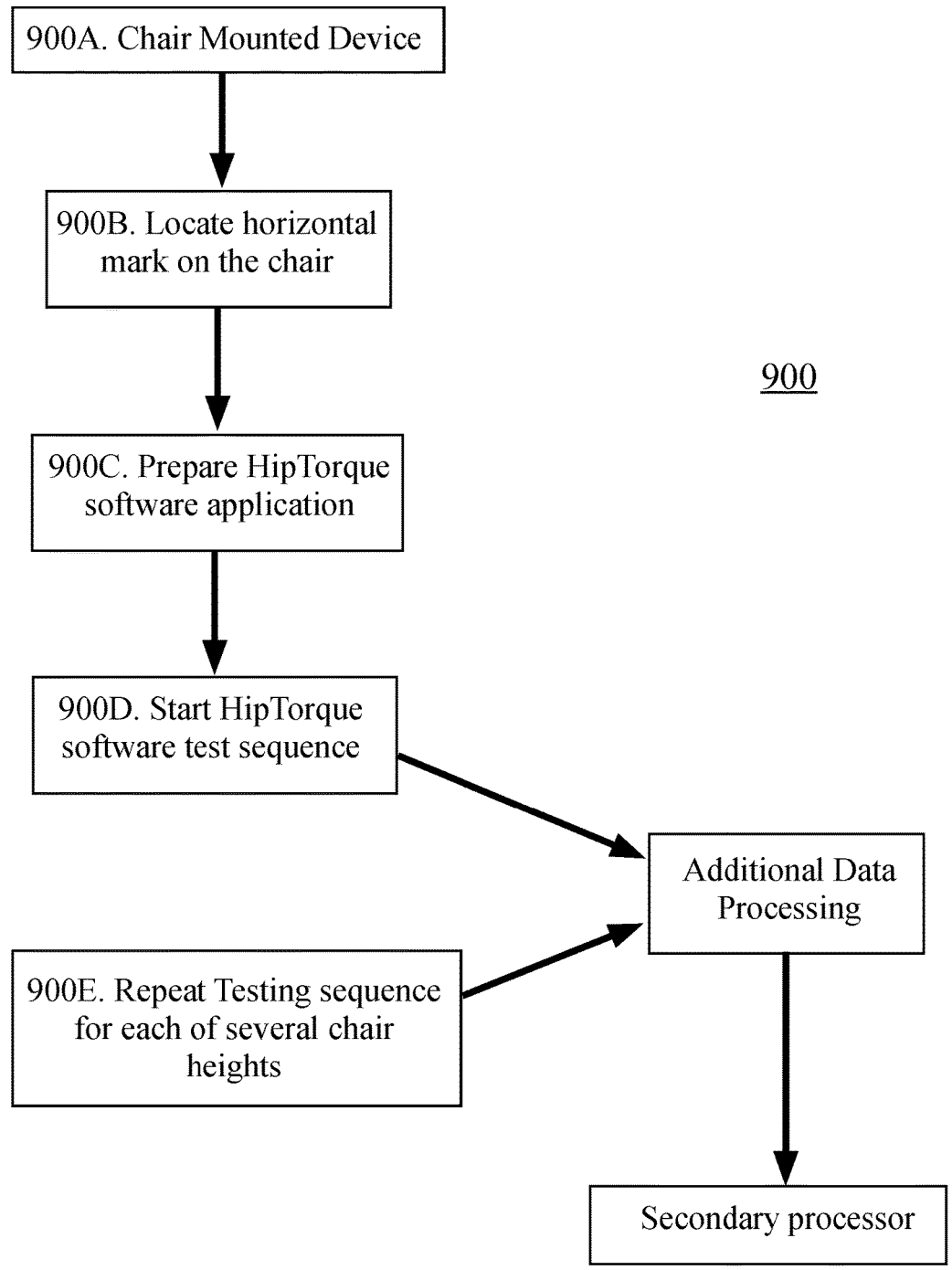
FIG. 9 depicts a flow chart of processes according to an embodiment of this invention for measuring hip torque.

FIG. 9 depicts a flow chart 900 showing further details shown in FIG. 8B. Diagonal movements, rather than fore-aft or side-side may be substituted. Input accelerometer data output into memory. First, Chair-Mounted Device 900A includes accelerometers for x, y, and z axes, primary processor, dedicated memory, operating system, software protocol (code), display (visual, auditory, vibration), keypad, Bluetooth wifi or wired connections, as indicated.

Then, also as depicted in FIG. 9, locate horizontal mark on chair (900B) to identify height of the ischial tuberosities and subsequent chair height. Then, in Step 900C, prepare HIPTORQUE™ program variables. Next, enter ID data, testing details as needed, choose static or dynamic test, and initial chair height. Testing details may be previously or automatically loaded by email or remote connection. They may include client profile: name, date, shift, location, job, tasks, PPE. Details may also include chair, caster/floor compatibility, shoe height, chair fit, features, design. Details may include workstation, surface area, shape, height, design, visual targets, reach distances, products, equipment, work tools, and task frequency.

Also as depicted in FIG. 9, prepare HIPTORQUE™ Software (900C). First, manually press start (900D), then subject moves chair in static or dynamic pattern with feet firmly on floor, next, the subject stops chair height test on completion of data set, indicated by the device display or tester. Then, manually press stop button. Also as depicted in FIG. 9, Repeat Testing Sequence (900E) for each of several chair heights. First, manually enter each measured chair pan height into the application and run HIPTORQUE™ program at each height. Next, record or file acceleration data for that height. Next, the device will indicate optimal height with visual or auditory display. Next, press reset button, repeat last two trials to confirm optimal height with second display of optimal height. Acceleration data is indicated for the chair height on the display. Using Additional Data Processing, data is either recorded by the tester or the value is automatically entered into the device database or Secondary Processor.

Example 4: Determining Optimal Seated Posture I

When the chair height is to be tested, start a leg strength application protocol, such as HIPTORQUE™ previously loaded onto an iPhone®, Android® device, other smart phone, or accelerometer-equipped device with a computerized processing system. One or more of the following can be implemented.

1. Attach the accelerometer/processor/device to the chair in a stable manner described previously, or using attachment with clamp, elastic or permanent fitting to the chair. The same location and orientation of the device on the chair should be maintained throughout the same testing sequence for comparable data sets with the same subject.

2. Locate a mark on the chair to approximate the height of the subject ischial tuberosities in sitting presuming compression of the upholstery. The distance from the same chair height landmark to the floor will be used for subsequent chair height measures.

3. Open the client software testing protocol on the device.

4. Enter subject identifiers: date and time (date and time may be entered automatically).

5. Record any pertinent descriptors for the particular test, ie, "office chair on linoleum," "subject's regular chair," "four-inch heels," "testing stool," etc.

6. Measure the selected chair height using the chair landmark that approximates the height for the ischial tuberosities and the distance to the floor.

7. Enter the measured chair height as the first entry in the subject test data.

8. Select Static or Dynamic testing protocol.
  a. Static protocol: Subject remains seated upright on the level chair pan, and is challenged with resisted movements of the arms while holding the chair steady.
  b. Dynamic protocol: Subject remains seated upright on the chair pan using resisted movements of the legs to move the chair.

9. Start the data collection process with a signal to the processor: press the 'Start' button, ask the subject to move the chair front-back and side-side for leg strength testing, and consider substituting other functional movements as indicated. Approximate work task postures and movement where possible. Ask the subject to stop the chair movement when the processor has collected sufficient data (5-10 seconds, or at a regular interval determined and signaled by the processor). Press the 'Stop' button.

10. Move the chair up or down to a second height, and measure the distance from the chair height landmark to the floor; record that height in the processor subject test protocol.

11. Repeat the data collection process for that chair height.

12. Repeat each chair height test and recording into the application sequence.

13. The processor can display several measured chair heights and acceleration numbers. Ask the subject to pick their 'best' height to compare subjective and objective measures.

14. Select optimal seat pan height for client, using either the subjective choice of pan height, or compare with the objective measures of acceleration for a suitable height with HIPTORQUE™ tool).

15. Position seat pan to forward or reclined angle (determined by prior postural observation) to support neutral spine posture in the working posture (identified using the HIPINDEX™ tool, then move chair back to support the torso.

16. Repeat the accelerometer data collection to confirm suitable pan height and angle. Differences in chair design may change seat pan height with pan angle, and may change the leg mechanics and strength.

Example 5: Measuring Seated Eye Height and Visual Targets

Eye height can be measured from the floor with a level line from the two eyes and the tape measure perpendicular to the floor. The monitor top line height can be positioned at the height of eye if no eyewear correction is used, or 3-4 inches below eye height for multi-focal lenses to preserve neutral spine postures at the neck.

The distance from the monitor to the eye can be selected with the usual considerations for focal length, screen image modifications (monitor orientation and position relative to neck rotation, dominant eye, angle of the monitor, contrast, brightness, color selection, calibration, font size, optimal refresh rate if CRT screen, ambient and incident lighting intensity and glare control as needed) with intent to preserve appropriate spinal postures.

The selected spinal postures in sitting were determined when the chair was adjusted as above, and the work surface height was established. The subject was then observed using the monitor and visual targets during the work process. Perturbations in the neutral head and neck postures during the work routine required modification of the image or the location of the target to preserve that posture. If the head moved forward, we improved the image quality to reduce glare at the surface of the monitor, positioned the monitor orientation closer to or tangent to the eye, reviewed the contrast, brightness and color settings for the monitor, increased the font size for the image or repositioned the target in the monitor field, moved the monitor closer to the eye, or recommended the need for vision correction. If present, visual fatigue required adjusting of the level of ambient light, minimizing adjacent or distracting light sources, or increasing the monitor distance from the eye while maintaining neutral neck postures.

Example 6: Determining Optimal Seated Posture II Optimal Elbow and Support Surface Heights, and Reach Distances After desired seated postures were identified and supported by the chair, measurements taken from the subject's anatomical landmarks were used to determine optimal locations for the work surface and work equipment. This can be done using one or more of the following steps:
1. The seated elbow height was measured with the hands laced together in a relaxed position in front of the upright torso relaxed against the back of the chair. The elbow height was measured from the point of the elbow (olecranon process) to the floor.
2. The dimensions of the elbow height with a relaxed shoulder was determined for the work surface height for typical keyboard and work surface activity, and was generally about one inch above the elbow height. A physical test to clarify variations in that height was to allow the level forearm to rest fully on the work surface with scapular depression, but without forward bending at the thoracic spine.
3. Several work surface heights were tested using available surfaces for forearm support in a proper chair, duplicating the work tasks. We observed shoulder posture using forearm support at about:
　a. Two inches above elbow height;
　b. One inch above elbow height;
　c. At the elbow height.
4. Where work surface height could not be reasonably adjusted, we used a stable foot support having sufficient area that allowed wide foot position and leg movement and relocated the chair and support postural correction from the chair; measured the desired vertical height from the floor to the adjusted chair pan, and provided that distance from the top of the foot support to the chair pan; then provided the selected work surface height.
5. We located the most frequently used work equipment and visual targets, either mounted above, below or on the work surface, with the most frequent, primary reach targets closer and minimized shoulder and torso movement. Near and far reach distances were established and determined by subject anthropometry, static and dynamic loads and frequency of reach.
6. Adjust chair armrest height and width:
　a. We adjusted chair armrest height to just under the work surface so that chair armrests did not impede moving the chair closer to the work surface and allowed full forearm support on the work surface. Armrest height and width allowed forearm support on the armrests when the chair was moved away from the work surface or reclined, maintaining desired scapular and thoracic mechanics.
　b. We positioned the armrests at a height of the work surface to support desired shoulder posture.
7. We adjusted the keyboard tray and arm after the subject was in an upright, seated posture. Some of the following steps were useful to choose a keyboard tray.
　a. We provided a keyboard tray and arm articulated for height and angle when a sustained, fully dedicated keyboard task exceeded minimal threshold use being uninterrupted keyboard use at maximal speed for more than 25 minutes, 3-4 times daily, with visual cues to the keyboard less than 1-2 times per minute.
　　i. We positioned the keyboard platform under the work surface height that was identified for surface work, above, which allowed for maximal height and angle range of motion of the keyboard platform.
　　ii. We positioned the keyboard tray below the height of the elbow, with tilt away from the user, and in line with the forearm and minimized wrist extension and free forearm movement for key-strike. Chair armrests should not impede the keyboard tray location to allow free elbow and forearm movement to enhance keystroke forces.
　　iii. We positioned the keyboard tray, arm and mouse for relaxed shoulder movement, neutral rotation at the shoulder and adequate palmar support with the wrist in neutral postures.

Multiple, mixed tasks on the work surface, combined with frequent, short keyboard entries, frequent visual cues to the keyboard and work surface, frequent or sustained shoulder reach to the work surface, or sustained use of a point-device were criteria to position the keyboard on the work surface at the proper height, naturally determined from optimal seated posture.

Example 7: Accelerometer Data Processing I

A software application ("app") was created to combine acceleration data, data storage and retrieval functions, and analytical methods to provide outputs to a user in visual format an a computer processor based device.
Environment
The app was developed with Corona SDK™ (www.coronalabs. com.). The programming language used was Lua. This environment was selected based on the need for very interactive and responsive user interface (UI), that would require displaying dynamic data and charts for rapid movements, so we selected the development platform used for creating games.

An alternative platform was considered, Appcelerator Titanium™. Although not selected for this Example, it had major improvements and current versions can be used as alternative to Corona SDK.

Description

The app measures the acceleration of a device or chair with a device attached thereto. The goal of the application was to measure maximum acceleration of a device chair, while making purposeful movements that demonstrate functional activity, left-right, forward-backward, or diagonally.

The app determines maximum acceleration in each direction, the total combined acceleration, and displays the information visually on the UI.

Use Cases

A person sits on the chair and makes purposeful movements, such as trying to move as quickly as possible using just the legs. The app is installed on the iPhone attached to the chair, or it could just lay down on the chair next to person, in a fixed position. The following steps can be carried out to run the app.

1. Pressing [Reset] and [Start] buttons activate acceleration tracking. Once the person makes the moves a maximum acceleration is displayed on the screen.
2. Pressing [Stop] button will pause tracking. The maximum acceleration value can be recorded in computer memory.
3. Adjust chair height and repeat the test, recording the chair height with maximum acceleration.
4. After a series of tests, the chair right with maximum acceleration would be selected as ideal height for the person.

Application Logic

To avoid errors, inconsistencies, or random noise, minor moves having accelerations of less than about 0.2 m/sec$^2$ were ignored. This number was set after preliminary experiments and proved to be sufficient to eliminate noise caused by minor movements.

The app assumed that a person can make non-linear moves in one direction, moving faster, then slower and faster again. The app logic will pick the single maximum acceleration from every move.

User Interface

Figure 10:
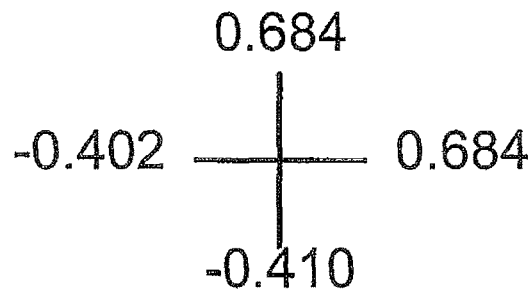
FIG. 10 depicts a Graphic User Interface (GUI) of an embodiment of this invention.

A Graphic User Interface (GUI) displays results of accelerations and seating conditions. One particular example is shown in FIG. 10, which depicts a drawing 1000 of an embodiment of this invention. The GUI displays the following information.

gravX—gravity in X direction
gravY—gravity in Y direction
gravZ—gravity in Z direction
accX—acceleration in X direction
accY—acceleration in Y direction
accZ—acceleration in Z direction
max X—max acceleration in X direction
max Y—max acceleration in Y direction
avr X—avr acceleration in X direction
avr Y—avr acceleration in Y direction
1.739—total max acceleration
1.037—total average acceleration

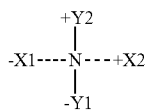

N—shows how many times maximum acceleration was exceeded in the current test
[Reset]—resets all numbers to 0
[Start]—starts acceleration tracking
Sounds Sounds play every time acceleration exceeds previous maximum. This may result in a series of sounds when making first move—as the acceleration will be reaching maximum for the first time. Subsequent moves will only play sound when maximum is exceeded, so user will be prompted via sound when the best moves are made.

Example 8: Accelerometer Data Processing II

Alternative Application Logic

The goal of this variation was to measure, collect and analyze the data about office chairs and optimize the chair settings for the individual needs of the users.

Measures

1. App collects accelerometer data from the phone
2. App checks the data at 30-60 frames per second
3. Multiple data values are collected:
   a. Max X acceleration
   b. Max Y acceleration
   c. Total Max acceleration
   d. Average X acceleration
   e. Average Y acceleration
   f. Etc.
4. Insignificant data, like minor moves of the phone, is ignored Data Collection Data is collected:
   a. For current user (multiple users)—optional
   b. Multiple sessions for each user (different dates)
   c. Multiple tests per user per session (dates)
   d. User ID/name are required to store data collected per user
   e. When application is launched, the optional prompt to enter/select the user is displayed
   f. For each session an optional chair name/parameters can be entered Application user can alternatively use paper notes to record the measurement from each session.

Data Analysis

1. Data analysis can be performed on the device OR
2. Data analysis can be performed on another server/device
   a. This can be done via manual data entry OR
   b. submission of data from the device to the server
3. If data is submitted to the server:
   a. the server receives the data with proper authorization/authentication
   b. Server stores the data associated with user
   c. Server can perform data analysis for this user
   d. Server can also perform data analysis by comparing data for similar users
4. Once data analysis is done, a recommendation can be displayed to the user using the be submitted via email or other channels.

Example 9: Photographic Analysis of Ergonomic Posture

In some embodiments, spine posture can be analyzed using photographic methods. In some of these embodiments, one can use a HIPPIC™ tool (a trademark of Fitzsimmons and Associates, Oakland, Calif.).

FIG. 11 depicts a drawing 1100 of a user seated at a workstation as seen through a camera, showing verical reference lines 140 at the bottom of the page aligned parallel to either the chair cylinder, table leg, or other vertical reference line. Angled reference lines 130 are shown radiating from a vertex, with the apex of the vertex depicted at the intersection of lines 105 and 110. Angled refererence lines 130 are shown at approximately 5° angles from each other. A photograph was taken, and the closest angle to line 110 was selected and marked on the photograph image with a stylus; the angle closest to the line to the ear 125 was marked on the image with a stylus; the resulting angle between lines 110 and 125 was then calculated by the processor as rearward bias for the torso, and the spinal bend was reported as minimal (<15 degrees) as shown. FIG. 11 shows the user in a desirable, spine neutral posture. The mid-point of angle A-B is approximately half of fifteen degrees or −7.5 degrees rearward bias, and the size of angle A-B is approximately 15 degrees, or minimal spinal bending. The image can be saved for comparison with subsequent images that represent changes in chair adjustment and work strategy.

FIG. 12 depicts a drawing 1200 of a user seated at a workstation as seen through a camera, showing verical reference lines 140 at the bottom of the page aligned parallel to either the chair cylinder, table leg, or other vertical reference line. Angled reference lines 130 are shown radiating from a vertex, with the apex of the vertex depicted at the intersection of lines 105 and 110. Angled refererence lines 130 are shown at approximately 5° angles from each other. A photograph was taken, and the closest angle to line 110 was selected and marked on the photograph image with a stylus; the angle of the line closest to the ear 125 was marked on the image with a stylus; the resulting angle between lines 110 and 125 was then calculated by the processor as forward bias of the torso, and the spinal bend reported as maximal (>20 degrees) for the lumbar spine. Angles observed greater than 20 degrees suggest further accommodation of the work and seating posture is desired. As shown, the user is in a forward slumped posture. Midpoint of angle A-B is approximately five degrees forward or +5 degrees forward bias, and the size of angle A-B is approximately 30 degrees, or near maximum spinal bending. The image can be saved for comparison with subsequent images that represent changes in chair adjustment and work strategy.

Example 10: Alternative Accelerometer-Based Analysis of Posture

This Example describes a method of this invention to measure a person's flexibility when sitting in an office chair. The computer-implemented application uses accelerometer data provided by device sensors.

Modern smart phones include accelerometer sensors, providing gravity data in X, Y, Z directions. The data is available to applications via build-in APIs (Application Programing Interfaces) of the phone's operating system. All phones provide "raw" accelerometer data readings, like Gravity values in X, Y and Z directions.

Figure 13:
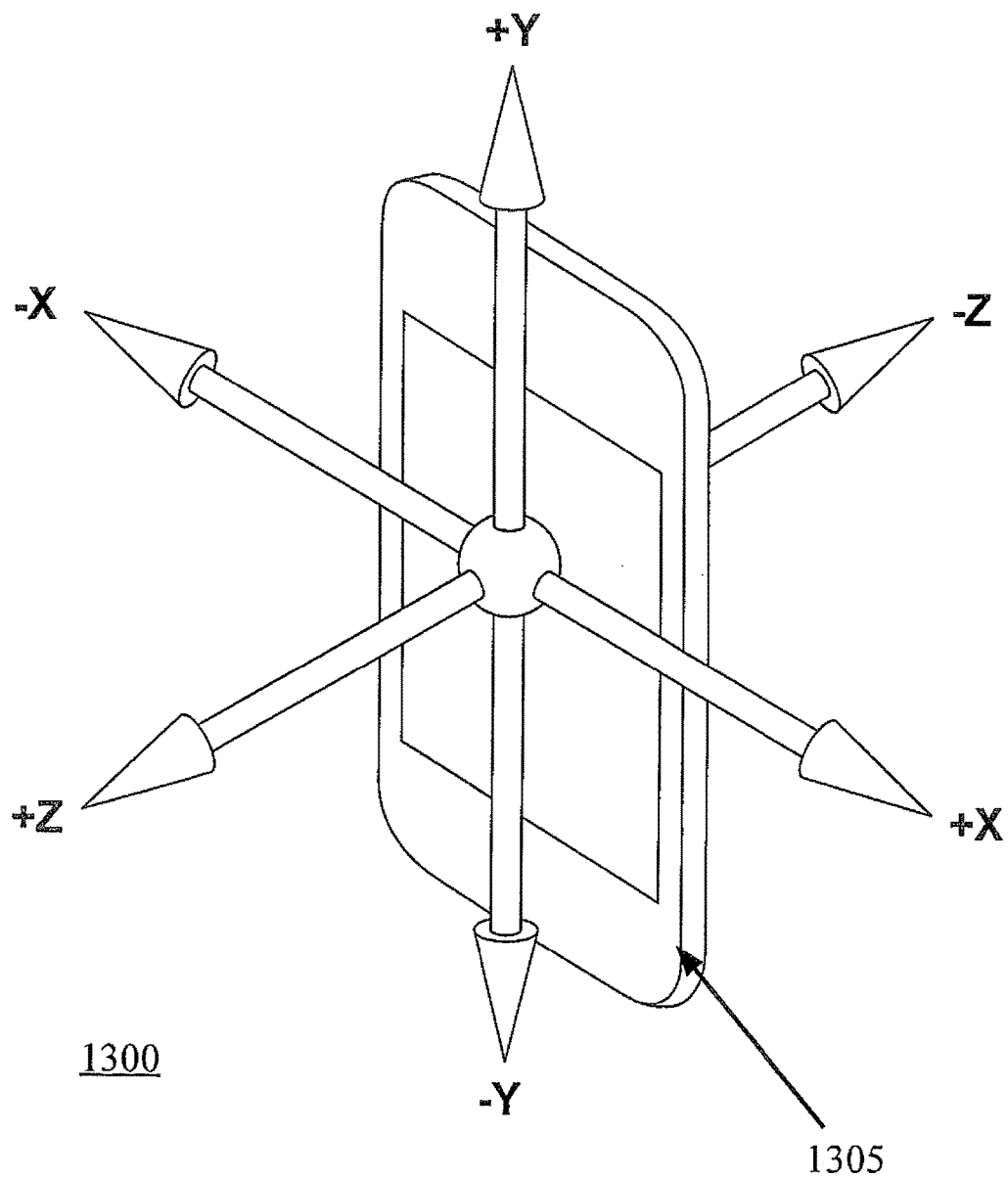
FIG. 13 depicts a drawing of a mobile device showing three (3) axes, X, Y, and Z for use in an embodiment of this invention.

FIG. 13 depicts an image 1300 of a mobile device 1305 showing three (3) axes of motion, X, Y, and Z. Motion in a positive direction is indicated by +X, +Y, and +Z, and motion in a negative direction is indicated by −Z, −Y, and −Z.

An accelerometer reports values for each axis in units of g-force, where a value of 1.0 represents acceleration of about +1 g along a given axis. When a device is laying still with its back on a horizontal surface, each acceleration event has approximately the following values:

x: 0
y: 0
z: −1

As used herein, these values are termed "gravX," "gravY," "gravZ," respectively. The values are averaged over time to derive reproducible data. Accelerometer data can be measured at a frequency of about 10 times a second. However, if desired, accelerometer data can be collected at longer intervals (e.g., 1, 2, 3, 4, 5, 6, 7, 8, or 9 times per second), or at shorter intervals (e.g., 12, 14, 16, 18, 20, 24, 30 or 40 times per second).

G-force data may not represent moving or acceleration of the device. For example, let's take the average of all gravity values:

$$G = (gravX^2 + gravY^2 + gravZ^2)^{1/2}$$

When the device is not moving, the value of G=1 is observed, regardless of orientation of the device. If we lift the phone and let it fall, then value of G=0 is observed while the phone experiences "zero gravity."

The value of G can be useful for some applications, like jumping, improvements can be achieved by measuring acceleration for analysis of posture at a workstation.

Measurement of Acceleration

To measure acceleration "A" of a device (chair, when device is attached to the chair), we consider A to be the change of speed "V" over time t. When the device speed is not changing, then A=0. This applies when a device is either not moving at all, or when it's moving at a steady speed (V is not changing).

Thus, A=0 when device is not in motion or moves at constant speed, and A>0 when speed of device is changing (speeding up, or slowing down), where the symbol ">" means "greater than."

To measure the acceleration A of a device, we can use gravity values gravX, gravY, gravZ obtained from the accelerometer to calculate acceleration values in 3 axes. The terms are defined below.

"accX" means linear acceleration/deceleration in the X axis;
"accY" means linear acceleration/deceleration in the Y axis; and
"accZ" means linear acceleration/deceleration in the Z axis Each of the above values may be positive (acceleration) or negative (deceleration). Acceleration values are calculated as changes of gravity values. Because gravity measurements are received from accelerometer many times per second (depending on the frequency of data acquisition), the acceleration values can be calculated at the same frequency as well.

It can be desirable to use linear acceleration/deceleration value A, and it also can be desirable to measure A as often as it changes. Also, because the measurements of gravity data from accelerometer may not exact, we can use a low pass filter. Low-pass filters are described in the see references below, all of which are incorporated herein fully by reference.

Below are the calculations for acceleration. Here ev.x, ev.y, ev.z are new gravity data values received from an accelerometer. gravX, gravY, gravZ are previous values.

1. Isolate the force of gravity with a low-pass filter.

$$gravX = alpha*gravX + (1-alpha)*ev.x;$$

$$gravY = alpha*gravY + (1-alpha)*ev.y;$$

$$gravZ = alpha*gravZ + (1-alpha)*ev.z;$$

where "alpha" is a constant relating to the time interval of the low pass filter—how quickly the filter smoothes the data curve. Generally, alpha is between zero (0) and one (1). Preferably, alpha is between 0.1 and 0.9, more preferably between 0.2 and 0.8, still more preferably between 0.3 and 0.7, even more preferably between 0.4 ad 0.6, and yet more preferably 0.5.

2. Remove the gravity contribution with a high-pass filter.
3. The Total Linear acceleration A is found according to the following expression:

$$A = (accX^2 + accY^2 + accZ^2)^{1/2}$$

When a device is not moving, the value of A=0.

References:
P1 Apple iOS Accelerator
Android Sensor Data
Display of Results

Figure 14:
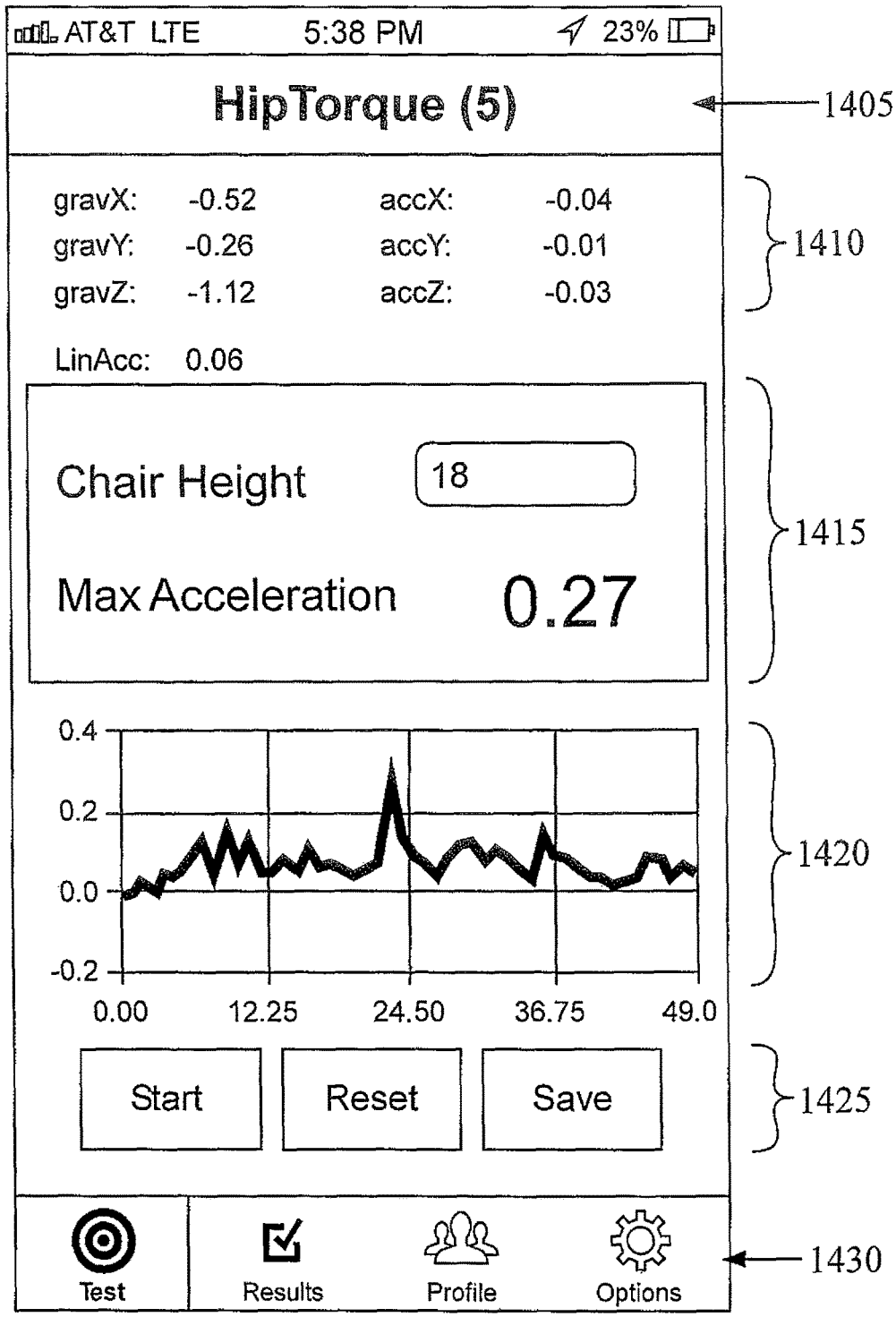
FIG. 14 depicts a dashboard view of a mobile device of an embodiment, showing results of analysis of acceleration of this invention of a subject seated at a workstation.

FIG. 14 depicts a drawing of a screen shot of a Graphical User Int4erface ("GUI") of a mobile device showing the application interface, including the values of gravX, gravY, gravZ, accX, accY, accZ, and linear acceleration ("LinAcc") an A value for every data update received from an accelerometer.

The application is designed to perform a number of repetitive tests for different chair height settings. The settings are not used for acceleration calculations, but are used to display and compare the acceleration values for different heights For each test, the device records liner acceleration and maximum acceleration A. The frequency of data received can be from about 1 to about 40 times per second, preferably about 10 times per second (and can vary depending on the mobile device used). Acceleration values are calculated and displayed as a chart of A values on the vertical (or x-axis) of the display screen versus time on the horizontal (or y-axis) of the display line The duration of each test can be generally between about 5 seconds to about 60 seconds.

User Protocol
User Steps for the Application
1. Launch application
2. Attach device on the chair, put it on the chair or hold it still in any other way, so the device accelerates/decelerates with the chair;
3. Enter chair height value (usually measured with a ruler);
4. Press the Start button;
5. Move the chair as fast as you can—in different directions, trying to achieve maximum acceleration;
6. Application will play sound every time max acceleration value is changed (new maximum is achieved);
7. After enough moves were made, either press Stop button (to stop recording), or wait for Auto-stop timer to automatically stop the recording (see Options screen for setting auto-stop time);
8. If you like the results—Press Save button. If not, press Reset button;
9. Repeat steps 3-8 as many times as needed;
10. Change chair height and repeat steps 3-9; and
11. After testing is complete, switch to Results screen to compare maximum Acceleration achieved for different chair heights.

The chair height with maximum acceleration is the optimal chair height for the user.

FIG. 14 depicts a representative dashboard 1400 for a series of accelerometer-based measurements of this invention. The information displayed are:
Device type, Time, Application Software version 1405;
Gravity (gravX, gravY, gravZ) is the current accelerometer data, accX, accY, accZ: the acceleration values 1410;
LinAcc: the Total Linear Acceleration (when there is no motion LinAcc=0.00); Chair Height and Maximum Acceleration value for current test 1415;
Graphical Display of Chart 1420 of Acceleration (vertical axis) versus time (horizontal axis) (obtained at a data capture rate of about 10 readings/second, but can be varied from about 1 per second to about 20 per second)
Buttons 1425: Start/Pause, Reset, Save.
Additional buttons 1430 are used to select features.
Optionally, sound plays when max Acceleration is updated.

Figure 15:
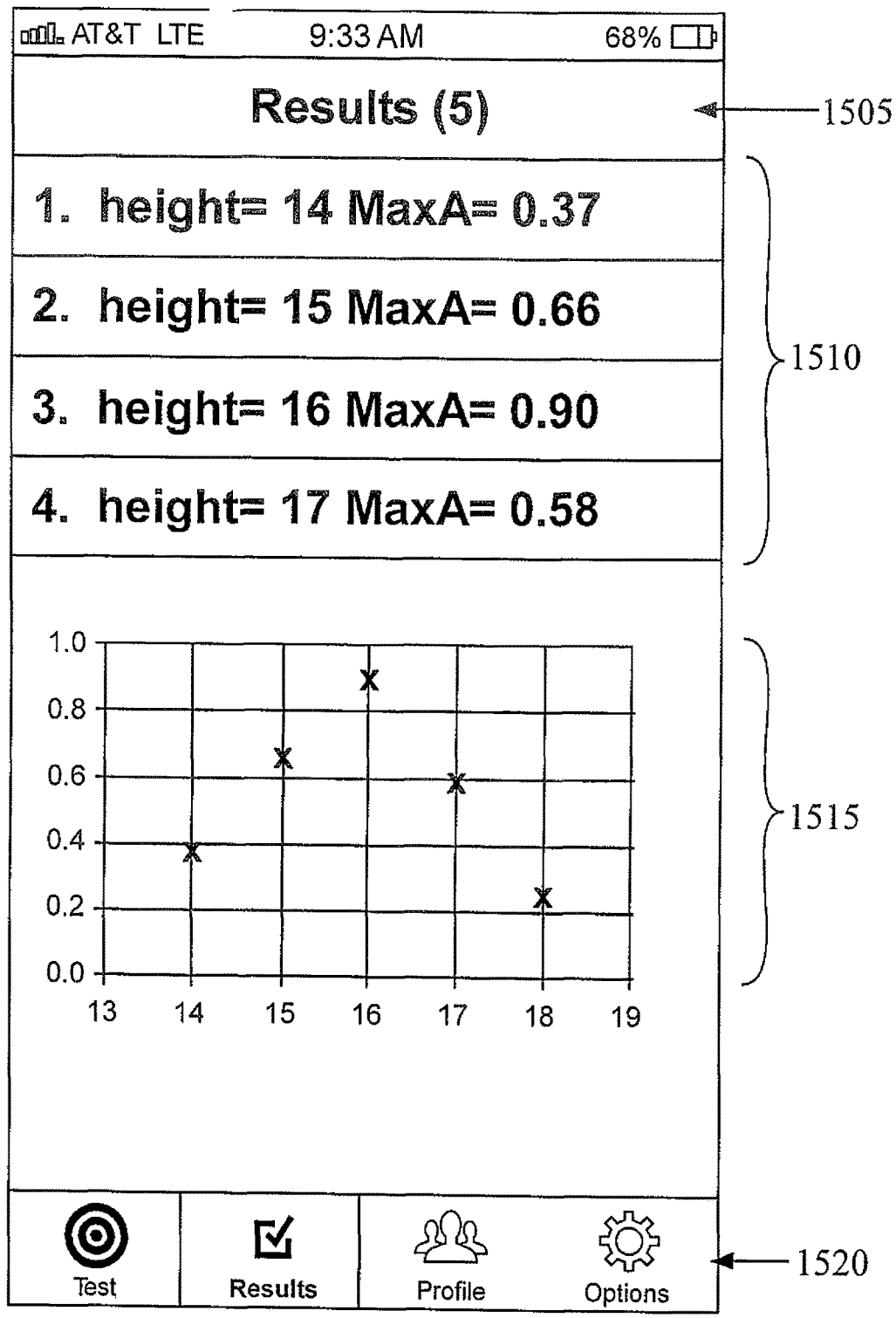
FIG. 15 depicts chair test results of an embodiment displayed on a mobile device showing a summary of results of this invention of a subject seated at a workstation.

FIG. 15 depicts a drawing of a screen shot 1500 of typical Summary Results of tests by a user using the devices and methods of this invention. Results of acceleration are depicted for four (4) different chair heights. The screen displays: (1) Header 1505 showing device type and time 1505, (2) Results 1510 for maximum acceleration ("MaxA") obtained at each chair height, (3) a graph ("Profile") 1515 of maximum acceleration (vertical axis) versus chair height (shown on horizontal axis), and (4) a series of control buttons 1520 at the bottom of the screen.

Figure 16:
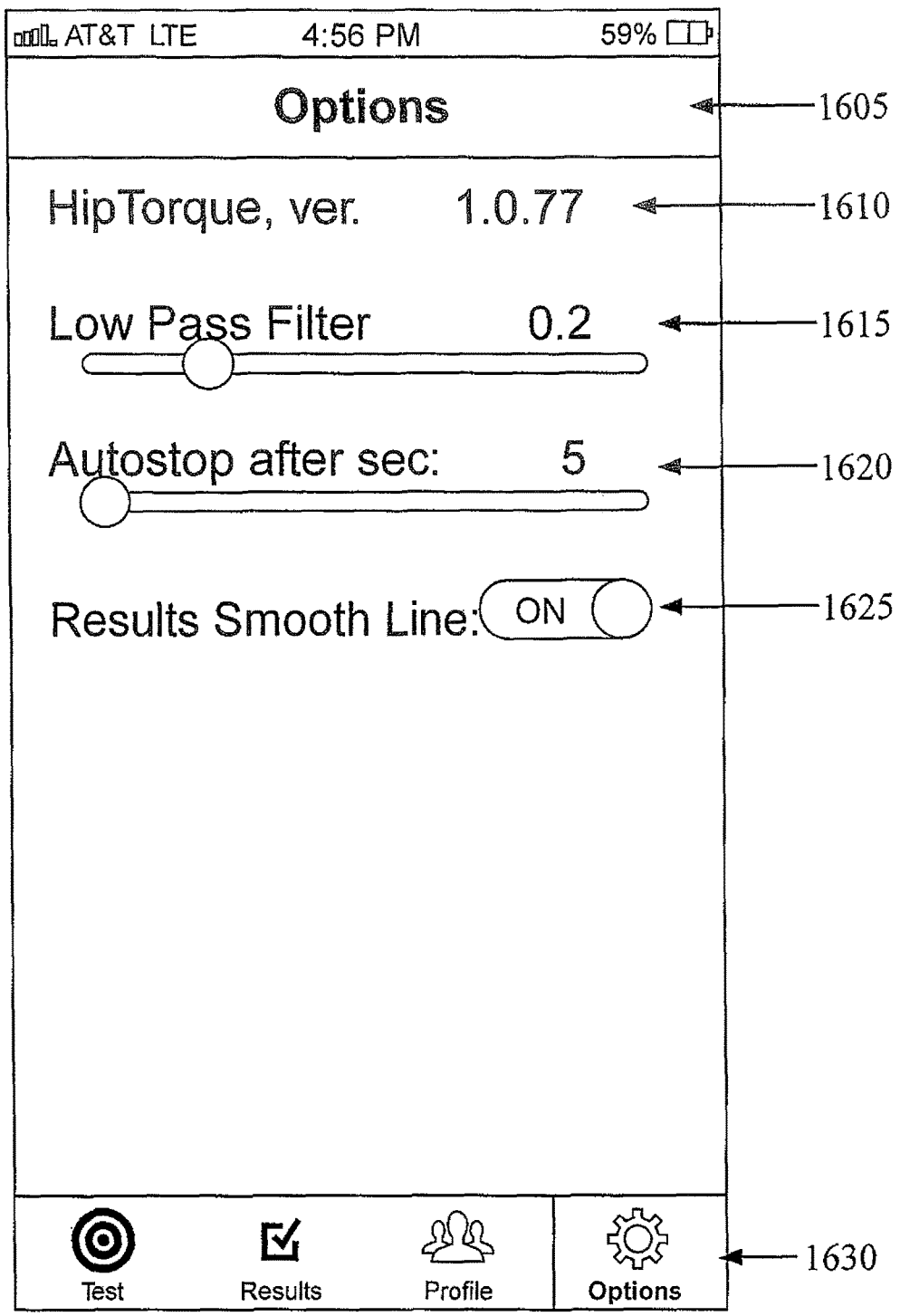
FIG. 16 depicts an option screen of an embodiment of a mobile device showing settings for filter, autostop time, and results.

FIG. 16 depicts a drawing of an Options Screen 1600 of a device of this invention. The information displayed includes: (1) header 1605 labeled Options, shown below device type and time, version of the HIPTORQUE™ software used 1610, (2) the setting 1615 of the low pass filter (this value can be changed by the user), (3) the time set 1620 for the Autostop feature, (4), whether the Results Smooth Line feature 1625 is ON or OFF, and (5) the control buttons 1630 on the bottom of the screen.

It can be appreciated that the descriptions herein represent only specific embodiments of the invention, and other embodiments can be created by persons of ordinary skill in the art without undue experimentation and with a likelihood of success. All such embodiments are considered to be part of this invention.

REFERENCES

Each of the references cited herein is incorporated fully by reference, as if separately so incorporated.

We claim:

1. A method for decreasing adverse spinal postures of a subject seated at a workstation, comprising the steps:
a) providing a mobile computing device, having a processor, a memory, a plurality of sensors for detecting acceleration; and a display;
b) affixing said mobile computing device to said chair:
c) adjusting the height of said chair to a first height and adjusting a seat pan angle to a first seat pan angle;
d) instructing said subject to sit in said chair and move the chair with maximum leg strength tested in functional directions, including forward-backward motion, side-to-side motion of the chair, and flexion and extension of the spine using said subject's feet placed firmly on the floor;
e) determining the maximum acceleration achieved during said moving in step d; where said determining maximum acceleration in step e is carried out by sensors and a processor, said processor programmed to perform the steps:

i) said sensors providing acceleration to sense and to provide gravity data for three dimensions of motion, an "X" dimension, a "Y" dimension, and a "Z" dimension, each of said dimensions being perpendicular to each of the other dimensions, said data being "gravX", "gravy", and "gravZ", respectively, each expressed as the effective gravitational acceleration in each of said dimensions;

ii) using said sensors to sample said gravity data at a frequency of 1 time per second to 40 times per second, filtering said data to reduce noise, storing said filtered data in said memory;

iii) updating said gravX, gravy and gravZ values where said updated values are calculated according to the following formulas:

$$gravX=alpha*gravX+(1-alpha)*ev.x;$$

$$gravY=alpha*gravY+(1-alpha)*ev.y;$$

$$gravZ=alpha*gravZ+(1-alpha)*ev.z;$$

where alpha is a time interval for a low pass filter, ev.x, ev.y, and ev.z are new gravity data in the X, Y, and Z dimensions respectively, and alpha is between 0.1 and 0.9;

iv) calculate acceleration by removing the gravity contribution using a high-pass filter according to the following formulas:

$$accX=ev.x-gravX;$$

$$accY=ev.y-gravY;$$

$$accZ=ev.z-gravZ,$$

where accZ, accY, and accZ are accelerations in the X, Y, and Z dimensions, respectively; and v) calculating for each time point, total linear acceleration ("A") according to the formula:

$$A=(accX^2+accY^2+accZ^2)^{1/2};$$

vi) storing said values of A in said memory; and f) adjusting the height of said chair to a second height, or adjusting said seat pan angle to a second seat pan angle;

g) repeating steps d and e;

h) adjusting the height of said chair to a third height, or adjusting said seat pan angle to a third seat pan angle;

i) repeating steps d and e;

j) displaying on the display, the maximum accelerations achieved versus chair height; and k) adjusting the chair height to the height producing maximum acceleration or adjusting the seat pan angle to the seat pan angle producing the maximum acceleration, said chair height or said seat pan angle so adjusted thereby decreasing adverse spinal posture of said subject.

2. The method of claim 1, further comprising after step j) adjusting said seat pan angle to a fourth seat pan angle, repeating steps d) and e), and displaying on the display, the maximum accelerations achieved versus seat pan angle.

3. The method of claim 1, where sampling rate of said gravity data is a frequency of 10 times per second.

4. The method of claim 1, further comprising the steps: establishing chair/caster/floor conditions; and confirming neutral spine posture.

5. The method of claim 4, where said step of confirming neutral spine posture is carried out by measuring the angle inscribed by a first line connecting a lateral point on said subject's waist over the lumbar spine and said subject's shoulder, and a second line connecting a lateral point on said subjects waist over the lumbar spine to said subject's ear, where said angle inscribed is less than 20 degrees.

6. The method of claim 4, where said step of confirming neutral spine posture is carried out by the steps:

i taking a photograph of said subject seated in said chair; and ii comparing the angle inscribed between a vertical line from said floor and a line connecting a lateral point on said subject's waist over the lumbar spine and said subject's ear, where said angle inscribed is less than 15 degrees.

7. The method of claim 1, further comprising the steps: measuring the height of the elbow and the eye of said subject; and providing a keyboard tray at a location that maintains neutral spine posture.

8. The method of claim 1, wherein said memory includes, programming instructions for carrying out the following steps:

i. accepting data from said sensors providing acceleration to provide gravity data for two or three dimensions of motion, an "X" dimension, a "Y" dimension, and optionally, a "Z" dimension, each of said dimensions being perpendicular to each of the other dimensions, said data being "gravX", "gravy", and "gravZ", respectively, each expressed as the effective gravitational acceleration in each of said dimensions;

ii. sampling said gravity data at a frequency of about 1 time per second to about 40 times per second, filtering said data to reduce noise and storing said filtered data in said memory;

iii. updating said gravX, gravy and gravZ values where said updated values are calculated according to the following formulas:

$$gravX=alpha*gravX+(1-alpha)*ev.x;$$

$$gravY=alpha*gravY+(1-alpha)*ev.y;$$

$$gravZ=alpha*gravZ+(1-alpha)*ev.z;$$

where alpha is a time interval for a low pass filter, ev.x, ev.y, and ev.z are new gravity data in the X, Y, and Z dimensions respectively, where alpha is between 0.1 and 0.9;

iv. calculating acceleration by removing the gravity contribution using a high-pass filter according to the following formula:

$$accX=ev.x-gravX;$$

$$accY=ev.y-gravY;$$

$$accZ=ev.z-gravZ,$$

where accZ, accY, and accZ are accelerations in the X, Y, and Z dimensions, respectively; and v. calculating for each time point, total linear acceleration ("A") according to the formula:

$$A=(accX^2+accY^2+accZ^2)^{1/2}.$$

9. The method of claim 8, said computer programming instructions including the step of selecting alpha between 0.2 and 0.8.

10. The method of claim 8, said computer programming instructions including the step of selecting alpha between 0.3 and 0.7.

11. The method of claim 8, said computer programming instructions including the step of selecting alpha between 0.4 and 0.6.

12. The method of claim 8, said computer programming instructions include the step of selection alpha to be 0.5.

13. The computer programming instructions of claim 8, further comprising:
   a memory storage module;
   a user interface; and
   a display.

14. The method of claim 1, where alpha is between 0.2 and 0.8.

15. The method of claim 1 where alpha is between 0.3 and 0.7.

16. The method of claim 1, where alpha is between 0.4 and 0.6.

17. The method of claim 1, where alpha is 0.5.

* * * * *